(12) United States Patent
Johansen et al.

(10) Patent No.: US 10,150,781 B2
(45) Date of Patent: Dec. 11, 2018

(54) 2-OXOTHIATOLE COMPOUNDS HAVING ACTIVITY AS CPLA2 INHIBITORS FOR THE TREATMENT OF INFLAMMATORY DISORDERS AND HYPERPROLIFERATIVE DISORDERS

(71) Applicant: Avexxin AS, Trondheim (NO)

(72) Inventors: Berit Johansen, Oslo (NO); Marcel Sanderberg, Oslo (NO); Inger-Reidun Aukrust, Oslo (NO); George Kokotos, Athens (GR); Johan Evenäs, Lund (SE); Thomas Brimert, Lund (SE); Kildahl-Andersen Geir, Oslo (NO)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 15/501,141

(22) PCT Filed: Aug. 3, 2015

(86) PCT No.: PCT/EP2015/067836
§ 371 (c)(1),
(2) Date: Feb. 1, 2017

(87) PCT Pub. No.: WO2016/016472
PCT Pub. Date: Feb. 4, 2016

(65) Prior Publication Data
US 2017/0166589 A1  Jun. 15, 2017

(30) Foreign Application Priority Data

Aug. 1, 2014 (GB) .................................. 1413695.6

(51) Int. Cl.
C07D 513/04 (2006.01)
C07D 417/04 (2006.01)
C07D 277/56 (2006.01)

(52) U.S. Cl.
CPC ......... *C07D 513/04* (2013.01); *C07D 277/56* (2013.01); *C07D 417/04* (2013.01)

(58) Field of Classification Search
None
See application file for complete search history.

(56) References Cited

U.S. PATENT DOCUMENTS 3,894,152 A   7/1975  Pons et al.
4,855,310 A   8/1989  Murase et al.
(Continued)

FOREIGN PATENT DOCUMENTS

AU   2006326548 A1   6/2007
DE         2042504 A1   4/1971
(Continued)

OTHER PUBLICATIONS

Mete et al. Bioorg. Med. Chem. Lett. 21(10), (2011) p. 3128-33.*
Joie Garfunkle et al: Optimization of the Central Heterocycle of a-Ketoheterocycle Inhibitors of Fatty Acid Amide Hydrolase, Journal Medicinal Chemistry, 2008, vol. 51, No. 15, pp. 4391-4403.
Walter Reid 1-34, Liebigs Ann. Chem. J. Org. Chemistry,Nov. 1, 1957 (Nov. 1, 1957), pp. 200-544.
Angela M. Bernard et al: Palladium (0) Catalyzed Nucleophilic Substitution on 2-Cyclopropylidene-Phenoxy Ethanes, Synthetic Communications, vol. 27, No. 5, Mar. 1, 1997 (Mar. 1, 1997), pp. 709-723, XP055111880.
George A. Kraus et al: Halogen-Metal Exchange/Cyclization of Iodoketones: A Direct Synthesis of 3-Arylbenzofurans, Synlett, No. 16, Jan. 1, 2005 (Jan. 1, 2005), pp. 2504-2506.
Legrand G. Van Uitert et al: The Dissociation Constants of Beta-Diketones in Water-Diozane Solutions, The School of Chemistry and Physics, The Pennsylvania State College, Jan. 20, 1953, pp. 455-457.
Alfredo Ricci et al: Heteroacylsilanes: Synthesis and Synthetic Potentialities of New Nucleophilic Acylation Agents, The Journal of Organic Chemistry, vol. 50, no., Jan. 1, 1985, pp. 130-133.
(Continued)

Primary Examiner — Yong L Chu
(74) Attorney, Agent, or Firm — McCarter & English, LLP; Steven G. Davis

(57) ABSTRACT

A compound of formula (I')

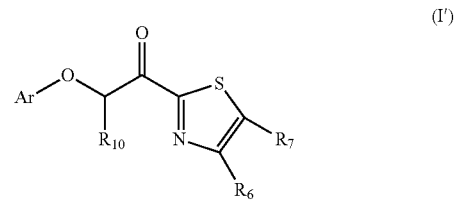

(I')

wherein $R_6$ is H, $C_{1-6}$alkyl, —$(CH_2)_p$COOH, —$(CH_2)_p$COO$C_{1-6}$alkyl, —$(CH_2)_p$CONH$_2$, —$(CH_2)_p$CONHC$_{1-6}$alkyl, —$(CH_2)_p$CON($C_{1-6}$alkyl)$_2$,
$R_7$ is as defined for $R_6$; or
$R_6$ and $R_7$ taken together with the atoms joining them can form a 6-membered aromatic or non aromatic, saturated or unsaturated, carbocyclic or heteroatom containing (e.g. O, N or S containing) ring optionally substituted by up to 4 groups $R_8$;
each $R_8$ is defined as for $R_6$ or is oxo;
$R_{10}$ is $C_{1-6}$ alkyl,
Ar is a $C_{6-14}$ aryl group, wherein the aryl group may be optionally substituted (preferably in the mew or para position relative to O) with one or more $R_9$ groups;
each $R_9$ is halo, OH, CN, nitro, NH$_2$, NHC$_{1-6}$alkyl, N($C_{1-6}$alkyl)$_2$, haloC$_{1-6}$alkyl, $C_{6-10}$ aryl group, $C_{7-12}$ arylalkyl, a $C_{1-10}$alkyl group, $C_{2-10}$-mono or multiply unsaturated alkenyl group, OC$_{1-10}$alkyl group, SC$_{1-10}$ alkyl group —OC$_{1-10}$alkyl-O—C$_{10}$alkyl, —C$_{1-10}$alkyl-O—C$_{1-10}$alkyl, —OC$_{2-10}$-mono or multiply unsaturated alkenyl group, OAr$^2$, O(CH$_2$)$_q$Ar$^2$, SAr$^2$ or S(CH$_2$)$_q$Ar$^2$;
wherein Ar$^2$ is phenyl, optionally substituted with one or more of halo, trihalomethyl, $C_{1-10}$-alkoxy, or $C_{1-10}$ alkyl;
each q is 1 to 3, preferably 1;
each p is 0 to 3;
or a salt, ester, solvate, N-oxide, or prodrug thereof.

1 Claim, No Drawings

(56) References Cited

U.S. PATENT DOCUMENTS

| | | | |
|---|---|---|---|
| 4,902,700 A | 2/1990 | Hayasi et al. | |
| 4,908,368 A | 3/1990 | Murase et al. | |
| 5,177,215 A | 1/1993 | Murase et al. | |
| 5,268,395 A | 12/1993 | Simandl et al. | |
| 5,272,986 A | 12/1993 | Smart | |
| 5,399,702 A | 3/1995 | Holland et al. | |
| 5,569,655 A | 10/1996 | Dority, Jr. et al. | |
| 5,569,665 A | 10/1996 | Porter et al. | |
| 5,658,909 A | 8/1997 | DeBernardis et al. | |
| 5,693,804 A | 12/1997 | DeBernardis et al. | |
| 6,214,994 B1 | 4/2001 | DeBernardis et al. | |
| 6,462,054 B1 | 10/2002 | Boger | |
| 7,056,917 B2 | 6/2006 | Nakayama et al. | |
| 9,597,318 B2 * | 3/2017 | Kokotos | A61K 31/421 |
| 2003/0055100 A1 | 3/2003 | Uckun et al. | |
| 2003/0130340 A1 | 7/2003 | Shimada et al. | |
| 2004/0041264 A1 | 3/2004 | Kloster et al. | |
| 2005/0137243 A1 | 6/2005 | Souers et al. | |
| 2005/0272036 A1 | 12/2005 | Barton et al. | |
| 2006/0016218 A1 | 1/2006 | Shapiro et al. | |
| 2011/0136879 A1 | 6/2011 | Kokotos et al. | |
| 2015/0376161 A1 | 12/2015 | Johansen et al. | |
| 2017/0166539 A1 | 6/2017 | Kokotos et al. | |

FOREIGN PATENT DOCUMENTS

| | | |
|---|---|---|
| EP | 03/51194 A2 | 1/1990 |
| EP | 0577003 A1 | 1/1994 |
| EP | 0735029 A1 | 10/1996 |
| EP | 0867437 A1 | 9/1998 |
| EP | 1201268 A2 | 5/2002 |
| EP | 1748044 A1 | 1/2007 |
| EP | 2116530 A1 | 11/2009 |
| GB | 1313150 A | 4/1973 |
| JP | 7-036069 | 2/1995 |
| JP | H11255700 A | 9/1999 |
| JP | 2001240593 A | 9/2001 |
| JP | 2005-128778 A | 5/2005 |
| WO | 93/07140 A1 | 4/1993 |
| WO | 96/03392 A1 | 2/1996 |
| WO | 96/15792 A1 | 5/1996 |
| WO | 96/16052 A2 | 5/1996 |
| WO | 96/36617 A1 | 11/1996 |
| WO | 96/036617 A1 | 11/1996 |
| WO | 96/39399 A1 | 12/1996 |
| WO | 98/32741 A1 | 7/1998 |
| WO | 00/09500 A2 | 2/2000 |
| WO | 00/34254 A1 | 6/2000 |
| WO | 01/00578 A1 | 1/2001 |
| WO | 2004/016609 A1 | 2/2004 |
| WO | 2004/033652 A2 | 4/2004 |
| WO | 2004/041264 A1 | 5/2004 |
| WO | 2004/041269 A2 | 5/2004 |
| WO | 2005/028456 A1 | 3/2005 |
| WO | 2005/028465 A1 | 3/2005 |
| WO | 2006/016218 A1 | 2/2006 |
| WO | 2006/057503 A1 | 6/2006 |
| WO | 2007/061862 A2 | 5/2007 |
| WO | 2007/070514 A1 | 6/2007 |
| WO | 2007/098142 A2 | 8/2007 |
| WO | 2008/013963 A2 | 1/2008 |
| WO | 2008107335 A1 | 9/2008 |
| WO | 2008/150492 A1 | 12/2008 |
| WO | 2011/039365 A1 | 4/2011 |
| WO | 2012/070420 A1 | 5/2012 |
| WO | 2014/118195 A1 | 8/2014 |

OTHER PUBLICATIONS

Antonio Mete et al: Design of novel and potent cPLA2a inhibitors containing an a-methyl-2-ketothiazole as metabolically stable serine trap, Bioorganic & Medicinal chemistry Letters 21 (2011) 3128-3133.

Vasudevan, Anil, et al., "Heterocyclic Ketones as Inhibitors of Histone Deacetylase", Bioorganic & Medicinal Chemistry Letters 13 (2003) 3909-3913.

1-Propanone, 3-phenyl-1-(2-thiazolyl); Registry No. 1179358-89-4; Entered STN: Sep. 2, 2009.

4-Thiazoleacetic acid, 2-[2-(3-methylphenoxy)acetyl]; Registry No. 927980-02-7; Entered STN: Mar. 23, 2007.

4-Thiazoleacetic acid, 2-[2-(2-naphthalenyloxy)acetyl]; Registry No. 927980-00-5; Entered STN: Mar. 23, 2007.

4-Thiazoleacetic acid, 2-[2-(2-methylphenoxy)acetyl]; Registry No. 927979-98-4; Entered STN: Mar. 23, 2007.

4-Thiazoleacetic acid, 2-(2-phenoxyacetyl); Registry No. 927979-96-2; Entered STN: Mar. 23, 2007.

4-Thiazoleacetic acid, 2-[2-[4-(1,1-dimethylethyl)phenoxy]acetyl]; Registry No. 927979-88-2; Entered STN: Mar. 23, 2007.

4-Thiazoleacetic acid, 2-[2-(2-ethoxyphenoxy)acetyl]; Registry No. 927979-82-6; Entered STN: Mar. 23, 2007.

4-Thiazoleacetic acid, 2-(2-[4-(1,1-dimethylpropyl)phenoxy[acetyl]; Registry No. 927979-60-0; Entered STN: Mar. 23, 2007.

4-Thiazoleacetic acid, 2-(2-(2-(1,1-dimethylethyl)phenoxylacetylJ; Registry No. 927979-42-8; Entered STN: Mar. 23, 2007.

4-Thiazoleacetic acid, 2-[2-(4-propylphenoxy)acetyl); Registry No. 927979-33-7; Entered STN: Mar. 23, 2007.

4-Thiazoleacetic acid, 2-[2[2-(1-methylethyl)phenoxy]acetyl]; Registry No. 927979-27-9; Entered STN: Mar. 23, 2007.

4-Thiazoleacetic acid, 2-[2[4-(1-methylethyl)phenoxy]acetyl]; Registry No. 927979-21-3; Entered STN: Mar. 23, 2007.

4-Thiazoleacetic acid, 2-[2-(3-methoxyphenoxy)acetyl]; Registry No. 927979-15-5; Entered STN: Mar. 23, 2007.

4-Thiazoleacetic acid, 2-[2-(4-methoxyphenoxy)acetyl]; Registry No. 927979-12-2; Entered STN: Mar. 23, 2007.

4-Thiazoleacetic acid, 2-[2-(4-ethylphenoxy)acetyll]; Registry No. 927975-68-6; Entered STN: Mar. 23, 2007.

4-Thiazoleacetic acid, 2-[2-(4-methylphenoxy)acetyll]; Registry No. 927975-65-3; Entered STN: Mar. 23, 2007.

4-Thiazolecarboxylic acid, 2-[2-(3-methylphenoxy)acetyl]; Registry No. 927975-62-0; Entered STN: Mar. 23, 2007.

4-Thiazolecarboxylic acid, 2-[2-(2-naphthalenyloxy)acetyl]; Registry No. 927975-60-8; Entered STN: Mar. 23, 2007.

4-Thiazolecarboxylic acid, 2-[2-(2-methylphenoxy)acetyl]; Registry No. 927975-57-3; Entered STN: Mar. 23, 2007.

4-Thiazolecarboxylic acid, 2-(2-phenoxyacetyl); Registry No. 927975-54-0; Entered STN: Mar. 23, 2007.

4-Thiazolecarboxylic acid, 2-[2[4-(1,1-dimethylethyl)phenoxy]acetyl]; Registry No. 927975-47-1; Entered STN: Mar. 23, 2007.

4-Thiazolecarboxylic acid, 2-[2-(2-ethoxyphenoxy)acetyl]; Registry No. 927975-41-5; Entered STN: Mar. 23, 2007.

4-Thiazolecarboxylic acid, 2-[2-[4-(1,1-dimethylpropyl)phenoxy]acetyl]; Registry No. 927975-25-5; Entered STN: Mar. 23, 2007.

4-Thiazolecarboxylic acid, 2-[2-[2-(1,1-dimethylethyl)phenoxy]acetyl]; Registry No. 927975-13-1.

4-Thiazolecarboxylic acid, 2-[2-(4-propylphenoxy)acetyl]; Registry No. 927975-07-3; Entered STN: Mar. 23, 2007.

4-Thiazolecarboxylic acid, 2-[2-[2-(l-methylethyl)phenoxylacetyl]; Registry No. 927975-03-9; Entered STN: Mar. 23, 2007.

4-Thiazolecarboxylic acid, 2-[2-[4-(1-methylethyl)phenoxyl]acetyl]; Registry No. 927974-99-0; Entered Mar. 23, 2007.

4-Thiazolecarboxylic acid, 2-[2-(3-methoxyphenoxy)acetyl]; Registry No. 927974-94-5; Entered STN: Mar. 23, 2007.

4-Thiazolecarboxylic acid, 2-[2-(4-methoxyphenoxy)acetyl]; Registry No. 927974-91-2; Entered STN: Mar. 23, 2007.

4-Thiazolecarboxylic acid, 2-[2-(4-,ethylphenoxy)acetyl]; Registry No. 927974-71-8; Entered STN: Mar. 23, 2007.

4-Thiazolecarboxylic acid, 2-[2-(4-methylphenoxy)acetyl]; Registry No. 927974-68-3; Entered STN: Mar. 23, 2007.

1-Propanone, 1,3-bis(2-benzothiazolyl); Registry No. 82605-58-1; Entered STN: Nov. 16, 1984.

Ahn, Kyunghye, et al., Novel Mechanistic Class of Fatty Acid Amide Hydrolase Inhibitors with Remarkable Selectivity, Biochemistry 2007, 46, 13019-13030.

(56) References Cited

OTHER PUBLICATIONS

Costanzo, Michael J., et al., Potent, Small-Molecule Inhibitors of Human Mast Cell Tryptase, Antiasthmatic Action of a Transition State Analogue Containing a Benzothiazole Ketone, J Med. Chem 2003, 46, 3865-3876.

Myllymaki, Mikko J., et al., Design, Synthesis, and In Vitro Evaluation of Carbamate Derivatives of 2-Benzoxazolyl-and 2-Benzothiazoly1-(3-hydroxyphenyl)-methanones as Novel Fatty Acid Amide Hydrolase Inhibitors, J. Med. Chem. 2007, 50, 4236-4242.

Allevi, Pietro, et al., Enzymatic Resolution of (R)- and (S)-2-(1-Hydroxyalkyl)thiazoles, Synthetic Equivalents of (R)- and (S)-2-Hydroxy Aldehydes, J. Org. Chem.996, 61, 4144-4147.

Chikashita, Hidenori, et al., General Reactivity of 2-Lithiobenzothiazole to Various Electrophiles and the Use as a Formyl Anion Equivalent in the Synthesis of a-Hydroxy Carbonyl Compounds, Bull. Chem. Soc. Jpn., 61, 3637-3648 (1998).

Schmidt, U. et al., Synthesis of Optically Active 2-(1-Hydroxyalkyl)-thiazole-4-carboxylic Acids and 2-(1-Aminoalkyl)-thiazole-4-carboxylic Acids, Journal of Synthetic Organic Chemistry, 1986, No. 12, pp. 2-8.

Martin, Thibaut, et al., Highly Efficient Borylation Suzuki Coupling Process for 4-Bromo-2-ketothiazoles: Straightforward Access to Micrococcinate and Saramycetate Esters, American Chemical Society, 2001, vol. 11, No. 16, pp. 3690-3693.

English language version of Chinese communication dated Mar. 20, 2013 issued in corresponding Chinese Patent Application No. 2010800560338.

B. Maryanoff et al., "Inhibitors of proteases and amide hydrolases that employ an a-ketoheterocycle as a key enabling functionality", Bioorganic & Medicinal Chemistry, vol. 16, pp. 1562-1595 (2008).

M. Seierstad et al., "Discovery and Development of Fatty Acid Amide Hydrolase (FAAH) Inhibitors", Journal of Medicinal Chemistry, vol. 51, No. 23, pp. 7327-7343 (2008).

International Search Report and written Opinion dated Jan. 17, 2011 in corresponding PCT Application No. PCT/EP2010/064687.

Marsilje, T.H et al, "Design, synthesis, and biological evaluation of simplified a-Keto heterocycle, trifluoromethyl Ketone, and formyl substituted folate analogues as potential inhibitors of GAR transformylase and AICAR transformylase" Bioorganic & Medicinal Chemistry, 2003, vol. 11, No. 20, pp. 4487-4501.

McGrath, M.E et al, "Structure-Guided Design of Peptide-Based Tryptase Inhibitors" Biochemistry, 2006, vol. 45, No. 19, pp. 5964-5973.

International Search Report and Written Opinoin dated Sep. 23, 2015 in corresponding PCT Application No. PCT/EP2015/067836.

Evans et al., Enantioselective Friedel-Crafts alkylations catalyzed by bis(oxazolinyl)pyridine-scandium(III) triflate complexes. J Am Chem Soc. Aug. 15, 2007;129(32):10029-41.

PubChem CID 9159507, AC1PLZGU, Oct. 8, 2016, 10 pages.

STN RN 10471-74-6, 1,3-Propanedione, 1-phenyl-3-(2-thienyl), Nov. 16, 1984, 1 page.

STN RN 1094445-68-7, 1,3-Propanedione, 1-(2-benzothiazolyl)-3-phenyl, Jan. 20, 2009, 1 page.

STN RN 1347363-73-8, Ethanone, 2-phenoxy-1-[6-(1H-pyrazol-4-yl)-2-benzothiazolyl], Dec. 2, 2011, 1 page.

STN RN 374754-17-3, Ethanone, 2-[(3-methoxyphenyl)thio]-1-(2-thiazolyl), Dec. 12, 2001, 1 page.

STN RN 882284-72-2, 2-Thiopheneacetic acid, 5-[2-(phenylthio)acetyl], Apr. 30, 2006, 1 page.

STN RN 927974-82-1, 4-Thiazolecarboxylic acid, 2-[2-(2,3-dimethylphenoxy)acetyl], Mar. 23, 2007, 1 page.

STN RN 927974-85-4, 4-Thiazolecarboxylic acid, 2-[2-(3,4-dimethylphenoxy)acetyl], Mar. 23, 2007, 1 page.

STN RN 927975-11-9, 4-Thiazolecarboxylic acid, 2-[2-[3-methyl-4-(1-methylethyl)phenoxy]acetyl], Mar. 23, 2007, 1 page.

STN RN 927975-29-9, 4-Thiazolecarboxylic acid, 2-[2-[2-(1,1-dimethylethyl)-4, Mar. 23, 2007, 1 page.

STN RN 927975-33-5, 4-Thiazolecarboxylic acid, 2-[2[4-(1-methyl-1-phenylethyl)phenoxy)acetyl], Mar. 23, 2007, 1 page.

STN RN 927975-52-8, 4-Thiazolecarboxylic acid, 2-[2-(4-clorophenoxy)acetyl], Mar. 23, 2007, 1 page.

CAS RN 1097121-81-7, 1,3-Propanedione, 1-(2-benzothiazolyl)-3-(4-methylphenyl)-, 2 pages.

\* cited by examiner

2-OXOTHIATOLE COMPOUNDS HAVING ACTIVITY AS CPLA2 INHIBITORS FOR THE TREATMENT OF INFLAMMATORY DISORDERS AND HYPERPROLIFERATIVE DISORDERS

This application is a National Phase application filed under 35 U.S.C. § 371 of PCT International Application No. PCT/EP2015/067836 with an International Filing Date of Aug. 3, 2015, which claims under 35 U.S.C. § 119(a) the benefit of Great Britain Application No. 1413695.6, filed Aug. 1, 2014, the entire contents of which are incorporated herein by reference.

The invention relates to certain new 2-oxothiazole compounds and to pharmaceutical compositions comprising said compounds. This invention also relates to the use of various 2-oxothiazole compounds for use in the prevention, treatment or alleviation of symptoms of chronic inflammatory disorders such as glomerulonephritis, rheumatoid arthritis and psoriasis as well as chronic inflammatory disorders associated with a diabetic condition in a patient, particularly diabetes mellitus, such as diabetic nephropathy and diabetic retinopathy. In another embodiment, this invention relates to the use of various 2-oxothiazole compounds for use in the prevention or treatment of hyperproliferative disorders such as cancer.

BACKGROUND

Mammalian cells contain a large number of phospholipases that hydrolyse phospholipids in a structurally specific manner for production of a myriad of products, many of which have potent biological activity. There has been considerable interest in characterising these enzymes because of their role in production of lipid mediators of inflammation. Since the first studies 20 years ago showing that mammalian cells contain a cystolic calcium dependent phospholipase A2 (cPLA2) specific for arachidonic acid, an extensive amount of evidence has substantiated a primary role for $cPLA_2$ as the key enzyme that mediates the release of arachidonic acid for the production of eicosanoids.

The enzyme $cPLA_2$ contributes to the pathogenesis of a variety of diseases particularly those in which inflammation plays a primary role implicating a role for inflammatory lipid mediators in disease pathogenesis. The inhibition therefore of such lipase enzymes offers a potential therapy for inflammatory conditions in particular chronic inflammatory conditions such as those above, psoriasis and glomerulonephritis.

The phospholipase A2s are a group of enzymes that release unsaturated fatty acids from the sn2 position of membrane phospholipids. Once released, the fatty acids are converted by various enzymes into biologically very important signalling molecules. Release of arachidonate initiates the arachidonate cascade leading to the synthesis of eicosanoids such as prostaglandins.

Eicosanoids are important in a variety of physiological processes and play a central role in inflammation. In Inflammation, Vol. 18, No. 1 1994, Andersen et al identify the presence of certain phospholipase A2s in psoriatic human skin.

It is therefore believed that inhibition of phospholipase A2 enzymes should have potential in curing some of the inflammatory symptoms, including epidermal hyperproliferation due to increased leukotriene production, related to eicosanoid production and cell activation in both epidermis and dermis in psoriasis.

Psoriasis is a common, chronic, inflammatory skin disorder. Psoriatic tissue is characterised by chronic inflammation in both epidermis and dermis, the disease being further characterised by hyperplasia of epidermal keratinocytes, fibroblast activation, alteration of eicosanoid metabolism, and leukocyte infiltration.

Glomerulonephritis, also known as glomerular nephritis, abbreviated GN, is a renal disease characterized by inflammation of the glomeruli, or small blood vessels in the kidneys. It may present with isolated hematuria and/or proteinuria or as a nephrotic syndrome, acute renal failure, or chronic renal failure. Glomerulonephritis is categorised into several different pathological patterns, which are broadly grouped into non-proliferative or proliferative types.

The glomerulus is a unique vascular network with three specialised types of cell: the endothelial cell, the mesangial cell and the visceral epithelial cell. Mesangial cells (MC) serve a number of functions in the renal glomerular capillary including structural support of the capillary tuft, modulation of the glomerular hemodynamics and a phagocytic function allowing removal of macromolecules and immune complexes. The proliferation of MC is a prominent feature of glomerular disease including IgA nephropathy, membranoproliferative glomerulonephritis, lupus nephritis, and diabetic nephropathy.

Reduction of MC proliferation in glomerular disease models by treatment with, for example, a low protein diet has been shown to produce extracellular matrix expansion and glomerulosclerotic changes. MC proliferation inhibitors may therefore offer therapeutic opportunities for the treatment of proliferative glomerular disease.

Mesangial proliferative glomerulonephritis is a form of glomerulonephritis which involves inflammation at the kidney glomeruli. The mesangial cells which are a part of the glomerular capillaries, increase in size giving the glomeruli a lumpy appearance. The disorder usually causes nephritic syndrome which represents protein loss in the urine. It may be present as acute, chronic or rapidly progressive glomerulonephritis and may progress to chronic renal failure.

The present inventors seek new treatments for, inter alia, chronic inflammatory conditions such as glomerulonephritis and associated conditions like diabetic nephropathy and retinopathy, psoriasis, dermatitis, rheumatoid arthritis and hyperproliferative disorders such as cancer.

SUMMARY OF THE INVENTION

The present inventors have surprisingly found that certain 2-oxothiazoles are ideal $cPLA_2$ inhibitors and offer new therapeutic routes to the treatment of chronic inflammatory disorders.

2-oxothiazole type structures are not new. In Bioorganic and Medicinal Chemistry 16 (2008) 1562-1595, there is a review of chemistry in this field. 2-oxo (benz)thiazoles carrying peptides or amino acids on the 2-position (i.e. where the 2-oxo group forms part of the backbone of an amino acid) are known in the art as thrombin inhibitors.

Also reported are certain hydrolase and transferase inhibitors in particular having a 2-oxo-oleyl side chain. Similar compounds as fatty acid amide hydrolase inhibitors are reported in J Med Chem Vol. 51, No. 237329-7343. Their potential as inhibitors of $cPLA_2$ is not discussed.

In a further aspect, the present inventors have also found that the compounds of the present invention offer value in the prevention or treatment of hyperproliferative disorders (defined below) such as cancer.

Thus, viewed from one aspect the invention provides a compound of formula (I)

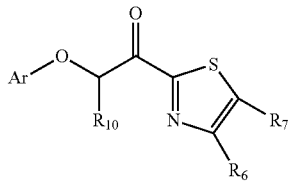

(I)

wherein $R_6$ is H, $C_{1-6}$alkyl, —$(CH_2)_p$COOH, —$(CH_2)_p$COOC$_{1-6}$alkyl, —$(CH_2)_p$CONH$_2$, —$(CH_2)_p$CONHC$_{1-6}$alkyl, —$(CH_2)_p$CON(C$_{1-6}$alkyl)$_2$, $R_7$ is as defined for $R_6$; or $R_6$ and $R_7$ taken together with the atoms joining them can form a 6-membered aromatic or non aromatic, saturated or unsaturated, carbocyclic or heteroatom containing (e.g. O, N or S containing) ring optionally substituted by up to 4 groups $R_8$;

each $R_8$ is defined as for $R_6$ or is oxo;

$R_{10}$ is $C_{1-6}$ alkyl,

Ar is a $C_{6-14}$ aryl group, wherein the aryl group may be optionally substituted (preferably in the mew or para position relative to O) with one or more $R_9$ groups;

each $R_9$ is halo, OH, CN, nitro, NH$_2$, NHC$_{1-6}$alkyl, N(C$_{1-6}$alkyl)$_2$, haloC$_{1-6}$alkyl, C$_{6-10}$ aryl group, C$_{7-12}$ arylalkyl, a C$_{1-10}$alkyl group, C$_{2-10}$-mono or multiply unsaturated alkenyl group, OC$_{1-10}$alkyl group, —OC$_{1-10}$alkyl-O—C$_{10}$alkyl, —OC$_{2-10}$-mono or multiply unsaturated alkenyl group, OAr$^2$, O(CH$_2$)$_q$Ar$^2$, SAr$^2$ or S(CH$_2$)$_q$Ar$^2$;

wherein Ar$^2$ is phenyl, optionally substituted with one or more of halo, trihalomethyl, C$_{1-10}$-alkoxy, or C$_{1-10}$ alkyl;

each q is 1 to 3, preferably 1;

each p is 0 to 3;

or a salt, ester, solvate, N-oxide, or prodrug thereof.

Viewed from another aspect the invention provides a compound of formula (II)

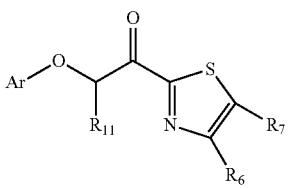

(II)

wherein $R_6$ is H, $C_{1-6}$alkyl, —$(CH_2)_p$COOH, —$(CH_2)_p$COOC$_{1-6}$alkyl, —$(CH_2)_p$CONH$_2$, —$(CH_2)_p$CONHC$_{1-6}$alkyl, —$(CH_2)_p$CON(C$_{1-6}$alkyl)$_2$, $R_7$ is as defined for $R_6$; or $R_6$ and $R_7$ taken together with the atoms joining them can form a 6-membered aromatic or non aromatic, saturated or unsaturated, carbocyclic or heteroatom containing (e.g. O, N or S containing) ring optionally substituted by up to 4 groups $R_8$;

each $R_8$ is defined as for $R_6$ or is oxo;

$R^{11}$ is H or $C_{1-6}$ alkyl;

Ar is a $C_{6-14}$ aryl group, wherein the aryl group is substituted (preferably in the mew or para position relative to O) with one or more $R_9$ groups;

each $R_9$ is —OC$_{1-10}$alkyl-O—C$_{1-10}$alkyl, OAr$^2$, O(CH$_2$)$_q$Ar$^2$, SAr$^2$ or S(CH$_2$)$_q$Ar$^2$;

wherein Ar$^2$ is phenyl, optionally substituted with one or more of halo, trihalomethyl, C$_{1-10}$-alkoxy, or C$_{1-10}$ alkyl;

each q is 1 to 3, preferably 1;

each p is 0 to 3;

or a salt, ester, solvate, N-oxide, or prodrug thereof.

Viewed from another aspect the invention provides a compound of formula (I')

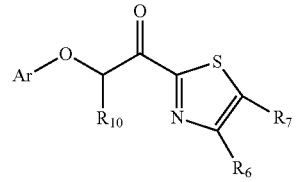

(I')

wherein $R_6$ is H, $C_{1-6}$alkyl, —$(CH_2)_p$COOH, —$(CH_2)_p$COOC$_{1-6}$alkyl, —$(CH_2)_p$CONH$_2$, —$(CH_2)_p$CONHC$_{1-6}$alkyl, —$(CH_2)_p$CON(C$_{1-6}$alkyl)$_2$, $R_7$ is as defined for $R_6$; or $R_6$ and $R_7$ taken together with the atoms joining them can form a 6-membered aromatic or non aromatic, saturated or unsaturated, carbocyclic or heteroatom containing (e.g. O, N or S containing) ring optionally substituted by up to 4 groups $R_8$;

each $R_8$ is defined as for $R_6$ or is oxo;

$R_{10}$ is alkyl,

Ar is a $C_{6-14}$ aryl group, wherein the aryl group may be optionally substituted (preferably in the mew or para position relative to O) with one or more $R_9$ groups;

each $R_9$ is halo, OH, CN, nitro, NH$_2$, NHC$_{1-6}$alkyl, N(C$_{1-6}$alkyl)$_2$, haloC$_{1-6}$alkyl, C$_{6-10}$ aryl group, C$_{7-12}$ arylalkyl, a C$_{1-10}$alkyl group, C$_{2-10}$-mono or multiply unsaturated alkenyl group, OC$_{1-10}$alkyl group, SC$_{1-10}$alkyl group —OC$_{1-10}$alkyl-O—C$_{10}$alkyl, —C$_{1-10}$alkyl-O—C$_{1-10}$alkyl, —OC$_{2-10}$-mono or multiply unsaturated alkenyl group, OAr$^2$, O(CH$_2$)$_q$Ar$^2$, SAr$^2$ or S(CH$_2$)$_q$Ar$^2$;

wherein Ar$^2$ is phenyl, optionally substituted with one or more of halo, trihalomethyl, C$_{1-10}$-alkoxy, or C$_{1-10}$ alkyl;

each q is 1 to 3, preferably 1;

each p is 0 to 3;

or a salt, ester, solvate, N-oxide, or prodrug thereof.

Viewed from another aspect the invention provides a compound of formula (II')

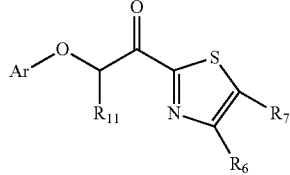

(II')

wherein $R_6$ is H, $C_{1-6}$alkyl, —$(CH_2)_p$COOH, —$(CH_2)_p$COOC$_{1-6}$alkyl, —$(CH_2)_p$CONH$_2$, —$(CH_2)_p$CONHC$_{1-6}$alkyl, —$(CH_2)_p$CON(C$_{1-6}$alkyl)$_2$, $R_7$ is as defined for $R_6$; or $R_6$ and $R_7$ taken together with the atoms joining them can form a 6-membered aromatic or non aromatic, saturated or unsaturated, carbocyclic or heteroatom containing (e.g. O, N or S containing) ring optionally substituted by up to 4 groups $R_8$;

each $R_8$ is defined as for $R_6$ or is oxo;
$R^{11}$ is H or $C_{1-6}$ alkyl;
Ar is a $C_{6-14}$ aryl group, wherein the aryl group is substituted (preferably in the mew or para position relative to 0) with one or more $R_9$ groups;
each $R_9$ is —$OC_{1-10}$alkyl-O—$C_{10}$alkyl, —$C_{1-10}$alkyl-O—$C_{1-10}$alkyl, $OAr^2$, $O(CH_2)_qAr^2$, $SC_{1-10}$alkyl, $SAr^2$ or $S(CH_2)_qAr^2$;
wherein $Ar^2$ is phenyl, optionally substituted with one or more of halo, trihalomethyl, $C_{1-10}$-alkoxy, or $C_{1-10}$ alkyl;
each q is 1 to 3, preferably 1;
each p is 0 to 3;
or a salt, ester, solvate, N-oxide, or prodrug thereof.

Viewed from another aspect the invention provides a compound of formula (III)

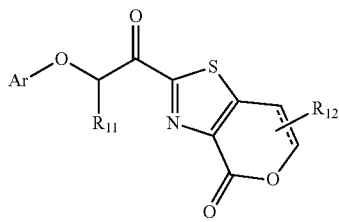

(III)

wherein $R_{11}$ is H or $C_{1-6}$ alkyl,
$R_{12}$ is H or $C_{1-6}$ alkyl;
Ar is a $C_{6-14}$ aryl group, wherein the aryl group may be optionally substituted (preferably in the mew or para position relative to O) with one or more $R_9$ groups;
each $R_9$ is halo, OH, CN, nitro, $NH_2$, $NHC_{1-6}$alkyl, $N(C_{1-6}alkyl)_2$, halo$C_{1-6}$alkyl, $C_{6-10}$ aryl group, $C_{7-12}$ arylalkyl, a $C_{1-10}$alkyl group, $C_{2-10}$-mono or multiply unsaturated alkenyl group, $OC_{1-10}$alkyl group, —$OC_{1-10}$alkyl-O—$C_{10}$alkyl, —$C_{1-10}$alkyl-O—$C_{1-10}$alkyl, —$OC_{2-10}$-mono or multiply unsaturated alkenyl group, $OAr^2$, $O(CH_2)_qAr^2$, $SAr^2$ or $S(CH_2)_qAr^2$;
wherein $Ar^2$ is phenyl, optionally substituted with one or more of halo, trihalomethyl, $C_{1-10}$-alkoxy, or $C_{1-10}$alkyl;
each q is 1 to 3;
the dotted line is an optional double bond;
or a salt, ester, solvate, N-oxide, or prodrug thereof.

Viewed from another aspect the invention provides a compound of formula (IV)

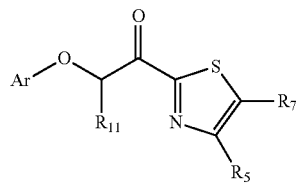

(IV)

$R_5$ is a heteroaryl or heterocyclic group such as furan, thiophene, pyyrole, pyrroline, pyrrolidine, oxazole, imidazole, imidazoline, imidazolidine, pyrazole, isooxazole, isothiazole, triazole, piperidine, pyridine, pyrimidine or thiazole optionally substituted with at least one group $R_{14}$ where $R_{14}$ is $C_{1-6}$ alkyl;

$R_7$ is H or $C_{1-6}$alkyl;
$R_{11}$ is H or $C_{1-6}$ alkyl,
Ar is a $C_{6-14}$ aryl group, wherein the aryl group may be optionally substituted (preferably in the mew or para position relative to $V_1$) with one or more $R_9$ groups;
Ar is a $C_{6-14}$ aryl group, wherein the aryl group may be optionally substituted (preferably in the mew or para position relative to O) with one or more $R_9$ groups;
each $R_9$ is halo, OH, CN, nitro, $NH_2$, $NHC_{1-6}$alkyl, $N(C_{1-6}alkyl)_2$, halo$C_{1-6}$alkyl, $C_{6-10}$ aryl group, $C_{7-12}$ arylalkyl, a $C_{1-10}$alkyl group, $C_{2-10}$-mono or multiply unsaturated alkenyl group, $OC_{1-10}$alkyl group, —$OC_{1-10}$alkyl-O—$C_{10}$alkyl, —$C_{1-10}$alkyl-O—$C_{1-10}$alkyl, —$OC_{2-10}$-mono or multiply unsaturated alkenyl group, $OAr^2$, $O(CH_2)_qAr^2$, $SAr^2$ or $S(CH_2)_qAr^2$;
wherein $Ar^2$ is phenyl, optionally substituted with one or more of halo, trihalomethyl, $C_{1-10}$-alkoxy, or $C_{1-10}$ alkyl;
each q is 1 to 3;
or a salt, ester, solvate, N-oxide, or prodrug thereof.

Viewed from another aspect the invention provides a compound as hereinbefore defined for use in therapy.

Viewed from another aspect the invention provides a compound as herein defined for use in the treatment of a chronic inflammatory condition.

Viewed from another aspect the invention provides a compound as herein defined for use in the treatment of a hyperproliferative disorder.

Viewed from another aspect the invention provides a pharmaceutical composition comprising a compound as hereinbefore defined.

Viewed from another aspect the invention provides a method of treating a chronically inflammatory disorder comprising administering to a patient in need thereof an effective amount of a compound as hereinbefore defined.

Viewed from another aspect the invention provides a method of treating a hyperproliferative disorder comprising administering to a patient in need thereof an effective amount of a compound as hereinbefore defined.

Definitions

In this specification, unless stated otherwise, the term "alkyl" includes both straight and branched chain alkyl radicals and may be methyl, ethyl, n-propyl, propyl, n-butyl, i-butyl, s-butyl, t-butyl, n-pentyl, i-pentyl, t-pentyl, neopentyl, n-hexyl or i-hexyl, t-hexyl. Any alkyl group is preferably linear.

The term "alkenyl" includes both straight and branched chain alkenyl radicals. The term alkenyl refers to an alkenyl radicals one or more double bonds and may be, but is not limited to vinyl, allyl, propenyl, i-propenyl, butenyl, butenyl, crotyl, pentenyl, pentenyl and hexenyl.

The term "aryl" refers to an optionally substituted monocyclic or bicyclic hydrocarbon ring system containing at least one unsaturated aromatic ring. Examples and suitable values of the term "aryl" are phenyl, naphtyl, 1,2,3,4-tetrahydronaphthyl, indyl, indenyl and the like.

The term arylalkyl covers aryl groups substituted with alkyl groups. The arylalkyl may bind to the carbon atom to which it is attached via the aryl ring or via a carbon of an alkyl substituent such as in benzyl.

Halo refers to fluoro, chloro, bromo or iodo, especially chloro or fluoro.

In any compound of the invention $R_9$ is preferably —$C_{1-10}$alkyl-O—$C_{10}$alkyl, —$C_{1-10}$alkyl-O—$C_{1-10}$alkyl, $OAr^2$, $O(CH_2)_qAr^2$, $SAr^2$ or $S(CH_2)_qAr^2$. $R_9$ may also be $SC1-10$alkyl.

DETAILED DESCRIPTION OF INVENTION

This invention relates to a series of related compounds which have utility in the treatment of chronic inflammatory disorders and hyperproliferative disorders.

Compounds of Formula (I) or (I')

In a first embodiment, the invention provides 2-oxothiazole compounds of formula (I) or (I')

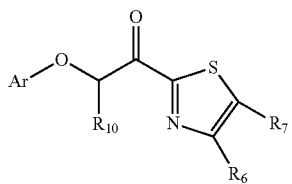

as hereinbefore defined or a salt, ester, solvate, N-oxide, or prodrug thereof.

In compounds of formula (I) or (I') it is preferred if $R_7$ is H.

$R_6$ is preferably H, $C_{1-6}$alkyl, —$(CH_2)_p$COOH, —$(CH_2)_p$CONH$_2$ or —$(CH_2)_p$COOC$_{1-6}$alkyl.

The subscript p is preferably 0 or 1. A most preferred option is —COOC$_{1-6}$alkyl.

$R_{10}$ is preferably methyl.

Ar is preferably phenyl.

In compounds of formula (I) there are preferably be 0, 1 or 2 groups $R^9$. Moreover, it is preferred if the substituents are positioned on adjacent carbon atoms, ideally the mew and para positions on the ring. Preferred options for $R_9$ are a $C_{4-10}$alkyl group, especially a $C_{6-8}$ alkyl group such as a $C_8$ alkyl group, a $C_{4-10}$ alkenyl group, a $OC_{1-10}$ alkyl group, —$OC_{1-10}$alkyl-O—$C_{10}$alkyl, —$C_{1-10}$alkyl-O—$C_{1-10}$alkyl, $C_{7-12}$ arylalkyl or a $C_{6-10}$ aryl group. $R_9$ may also be $SC_{1-10}$alkyl. $R_9$ alkyl groups are preferably linear.

A preferred structure is therefore formula (Ia)

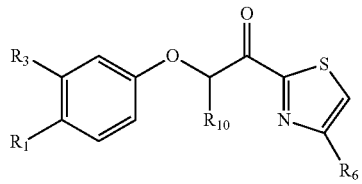

wherein $R_6$ and $R_{10}$ are as hereinbefore defined;

$R_1$ and $R_3$ are each independently selected from H, halo (e.g. fluoro or chloro), $C_{6-10}$aryl, $C_{7-12}$ arylalkyl, $C_{2-12}$ alkenyl; $OC_{1-10}$ alkyl, $C_{1-10}$—O—$C_{1-10}$ alkyl, $OC_{1-10}$—O—$C_{1-10}$ alkyl, $OC_{2-10}$ alkenyl or a $C_{1-10}$ alkyl group; or a salt, ester, solvate, N-oxide, or prodrug thereof. $R_1$ and $R_3$ may also be $SC_{1-10}$alkyl.

In compounds (Ia), it is preferred if one of $R_1$ and $R_3$, most preferably $R_1$, is a $C_{4-10}$alkyl group, especially a $C_{6-8}$ alkyl groups such as a $C_8$ alkyl group or a $C_{6-10}$ aryl group or —$C_{1-10}$alkyl-O—$C_{10}$alkyl. $R_1$ and $R_3$ are preferably different.

It is preferred if both $R_1$ and $R_3$ are not H.

It is preferred if one of $R_1$ and $R_3$ is a $C_{4-10}$alkyl group, $C_{2-10}$ alkenyl group or —$OC_{4-10}$ alkyl group and the other is H, halo or $OC_{1-6}$ alkyl.

$R_3$ is preferably H, halo or $OC_{1-6}$ alkyl. Alkyl groups are preferably linear.

Where $R_1$ or $R_3$ is alkenyl, it preferably contains one double bond. Ideally that double bond is on the two carbons nearest the Ar group.

Specifically preferred structures of formula (I) include:

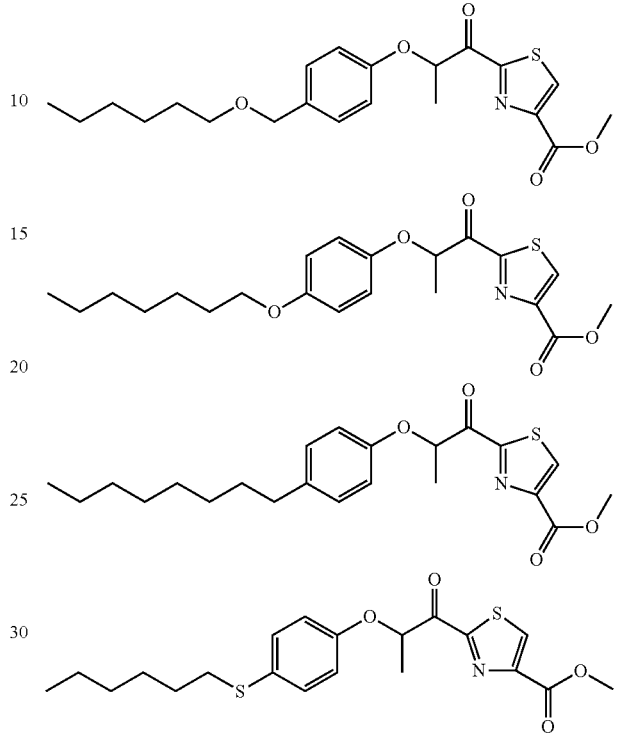

or salts thereof.

Compounds of Formula (II) or (II')

In a second embodiment, compounds of interest are of formula (II) or (II'):

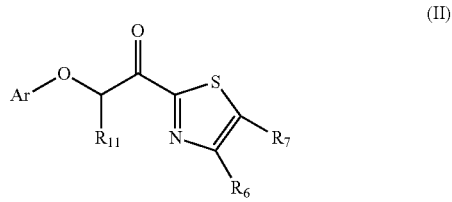

(II)

as herein before defined or a salt, ester, solvate, N-oxide, or prodrug thereof. In compounds of formula (II) or (II'), $R_7$ is preferably H.

$R_6$ is preferably H, $C_{1-6}$alkyl, —$(CH_2)_p$COOH, —$(CH_2)_p$CONH$_2$ or —$(CH_2)_p$COOC$_{1-6}$alkyl. The subscript p is preferably 0 or 1. A preferred option is —COOC$_{1-6}$alkyl.

$R_{11}$ is preferably H or Me, especially H.

Ar is preferably phenyl.

There is preferably one $R_9$ group present. The $R_9$ group is preferably para to the O atom. $R_9$ is preferably —$OC_{1-10}$alkyl-O—$C_{10}$alkyl, —$OAr^2$, —$S(CH_2)_qAr^2$ or —$O(CH_2)_qAr^2$. The subscript q is preferably 1 or 2, such as 1. $Ar^2$ is preferably Ph optionally substituted with F, $CF_3$ or OMe. There is preferably one substituent on the $Ar^2$ group. That substituent is preferably in the para position. Preferred groups —$OC_{1-10}$alkyl-O—$C_{10}$alkyl include —$OCH_2OC_{10}$alkyl. $R_9$ may also be $SC_{1-10}$alkyl.

Preferred compounds are therefore of formula (IIc)

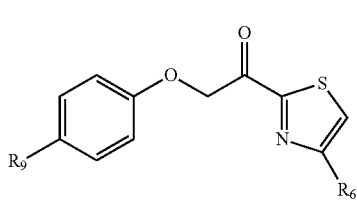

(IIc)

wherein $R_6$ is H, $C_{1-6}$alkyl, $-(CH_2)_p$COOH, $-(CH_2)_p$COOC$_{1-6}$alkyl, $-(CH_2)_p$CONH$_2$, $-(CH_2)_p$CONHC$_{1-6}$alkyl, $-(CH_2)_p$CON(C$_{1-6}$alkyl)$_2$, $R_9$ is $-OC_{1-10}$alkyl-O$-C_{10}$alkyl, $-OAr^2$, $-O(CH_2)_q$Ar$^2$, SAr$^2$ or S(CH$_2$)$_q$Ar$^2$ (or $R_9$ may also be SC$_{1-10}$alkyl);

wherein Ar$^2$ is phenyl, optionally substituted with one or more of halo, trihalomethyl, $C_{1-10}$-alkoxy, or $C_{1-10}$ alkyl;

each q is 1 to 3, preferably 1;

each p is 0 to 3;

or a salt, ester, solvate, N-oxide, or prodrug thereof. Alkyl groups are preferably linear.

Specific preferred compounds include those of formula (II″)

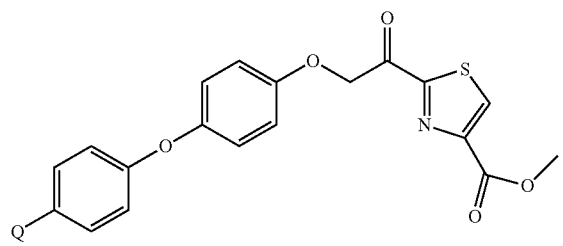

(II″)

wherein Q is H, F, CF$_3$ or OMe; or a salt thereof;
and compounds of formula (IIa) and (IIb):

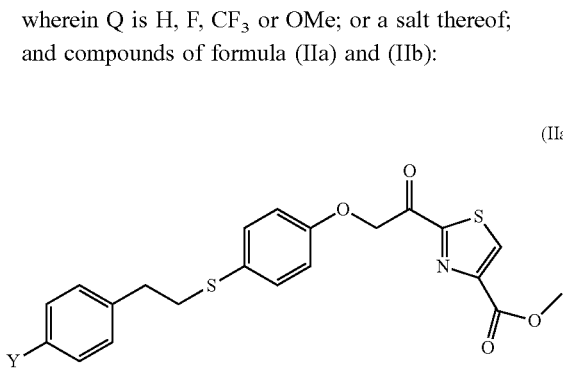

(IIa)

(IIb)

where Y is H, F, CF$_3$ or OMe; or a salt thereof.

Also preferred is

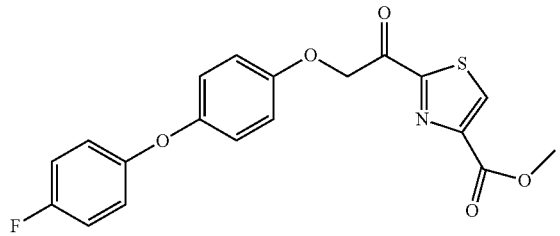 [SMILES: COC(=O)c1csc(C(=O)COc2ccc(Oc3ccc(F)cc3)cc2)n1]

or a salt thereof.
Compounds of Formula (III)
Further compounds of interest are of formula (III)

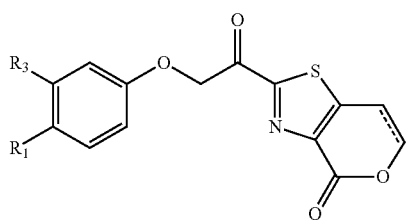

(III)

as herein defined or a salt, ester, solvate, N-oxide, or prodrug thereof.

It is preferred if $R_{11}$ is H.

It is preferred if $R_{12}$ is H or Me, preferably H.

Ar is preferably phenyl.

In compounds of formula (III) there may be 0, 1 or 2 groups R$^9$. Moreover, it is preferred if the substituents are positioned on adjacent carbon atoms, ideally the meta and para positions on the ring. Preferred options for $R_9$ are a $C_{4-10}$alkyl group, especially a $C_{6-8}$ alkyl group such as a $C_8$ alkyl group, a $C_{4-10}$ alkenyl group, a OC$_{1-10}$ alkyl group, $-C_{1-10}$alkyl-O$-C_{1-10}$alkyl, $C_{7-12}$ arylalkyl or a $C_{6-10}$ aryl group. $R_9$ alkyl groups are preferably linear.

A preferred structure is formula (III')

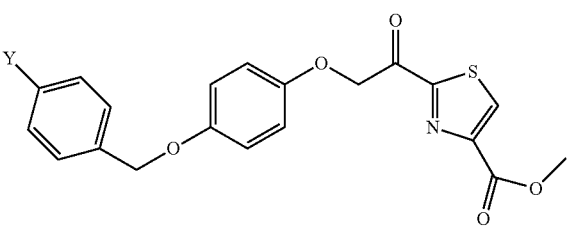

(III')

wherein $R_1$ and $R_3$ are each independently selected from H, halo (e.g. fluoro or chloro), $C_{6-10}$aryl, $C_{7-12}$ arylalkyl, $C_{2-12}$ alkenyl; OC$_{1-12}$ alkyl, OC$_{2-12}$ alkenyl or a $C_{1-12}$ alkyl group; or a salt thereof.

In compounds (III'), it is preferred if one of $R_1$ and $R_3$, most preferably $R_1$, is a $C_{4-10}$alkyl group, especially a $C_{6-8}$ alkyl groups such as a $C_8$ alkyl group or a $C_{6-10}$ aryl group or $-C_{1-10}$alkyl-O$-C_{1-10}$alkyl. $R_1$ and $R_3$ are preferably different. Alkyl groups are preferably linear.

It is preferred if both $R_1$ and $R_3$ are not H.

It is preferred if one of $R_1$ and $R_3$ is a $C_{4-10}$alkyl group, $C_{2-10}$ alkenyl group or $-OC_{4-10}$ alkyl group and the other is H, halo or OC$_{1-6}$ alkyl.

$R_3$ is preferably H, halo or $OC_{1-6}$ alkyl.

Where $R_1$ or $R_3$ is alkenyl, it preferably contains one double bond. Ideally that double bond is on the two carbons nearest the Ar group.

Specifically preferred options include

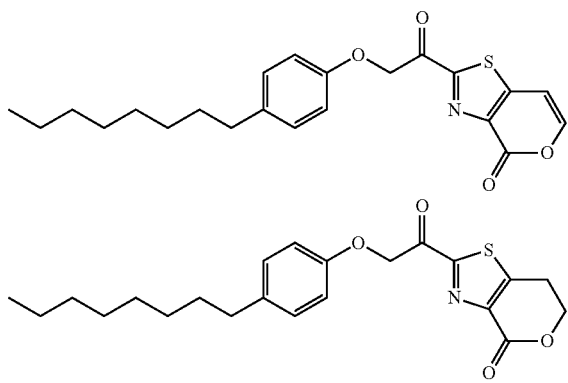

or salts thereof.

Compounds of Formula (IV)

In a further preferred embodiment, the invention relates to compounds of formula (IV) as hereinbefore defined

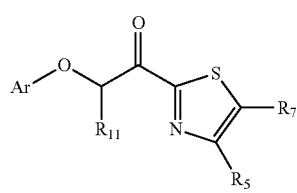

(IV)

or a salt thereof.

It is preferred if $R_5$ is an oxazole optionally substituted with $C_{1-6}$ alkyl. $R_5$ is preferably oxazole ideally where the oxazole is linked to the molecule via the carbon between the heteroatoms.

$R_7$ is preferably H.

$R_{11}$ is preferably H.

Ar is preferably phenyl.

In compounds of formula (I) there may be 0, 1 or 2 groups $R^9$. Moreover, it is preferred if the substituents are positioned on adjacent carbon atoms, ideally the meta and para positions on the ring. Preferred options for $R_9$ are a $C_{4-10}$alkyl group, especially a $C_{6-8}$ alkyl group such as a $C_8$ alkyl group, a $C_{4-10}$ alkenyl group, a $OC_{1-10}$ alkyl group, $C_{7-12}$ arylalkyl or a $C_{6-10}$ aryl group. $R_9$ alkyl groups are preferably linear.

A preferred structure is formula (IV')

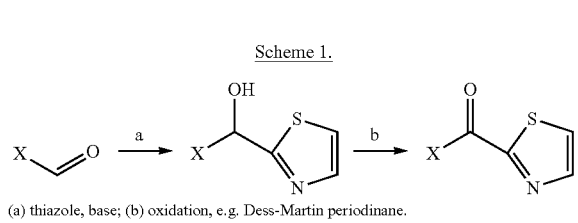

(IV')

wherein $R_1$ and $R_3$ are each independently selected from H, halo (e.g. fluoro or chloro), $C_{6-10}$aryl, $C_{7-12}$ arylalkyl, $C_{2-12}$ alkenyl; $OC_{1-12}$ alkyl, $OC_{2-12}$ alkenyl or a $C_{1-12}$ alkyl group; or a salt thereof.

In compounds (IV'), it is preferred if one of $R_1$ and $R_3$, most preferably $R_1$, is a $C_{4-10}$alkyl group, especially a $C_{6-8}$ alkyl groups such as a $C_8$ alkyl group or a $C_{6-10}$ aryl group. $R_1$ and $R_3$ are preferably different.

It is preferred if both $R_1$ and $R_3$ are not H.

It is preferred if one of $R_1$ and $R_3$ is a $C_{4-10}$alkyl group, $C_{2-10}$ alkenyl group or $-OC_{4-10}$ alkyl group and the other is H, halo or $OC_{1-6}$ alkyl. Alkyl groups are preferably linear.

$R_3$ is preferably H, halo or $OC_{1-6}$ alkyl.

Where $R_1$ or $R_3$ is alkenyl, it preferably contains one double bond. Ideally that double bond is on the two carbons nearest the Ar group.

Specifically preferred options include

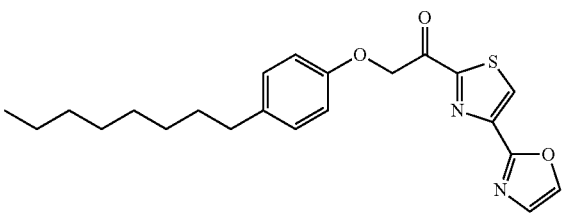

or a salt thereof.

Synthesis

The manufacture of the compounds of the invention typically involves known literature reactions. For example, the formation of a 2-oxothiazole, the precursor to many of the claimed compounds, can be achieved by reaction of an aldehyde XCOH with thiazole in the presence of a base and subsequent oxidation of the hydroxyl to a ketone. The X group is obviously selected to form the desired side chain group or a precursor thereof.

These reactions are summarised in Scheme 1 below.

Scheme 1.

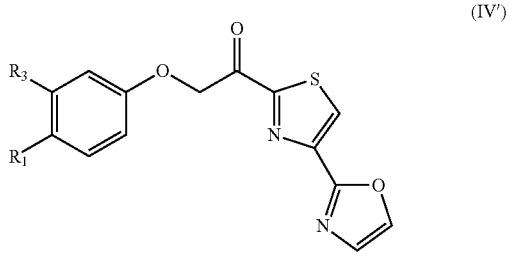

(a) thiazole, base; (b) oxidation, e.g. Dess-Martin periodinane.

It will be appreciated that in the scheme above and many of those below, specific reagents and solvents may mentioned to aid the skilled man in carrying out the reactions described. The skilled man will appreciate however that a variety of different conditions, reagents, solvents, reactions etc could be used to effect the chemistry described and the conditions quoted are not intended to be limiting on the reactions described.

An alternative strategy involves the reaction of an alkoxy amide XCON(Oalkyl) with thiazole in base which affords 2-oxothiazoles directly. This reaction is summarised in scheme 2.

Scheme 2.

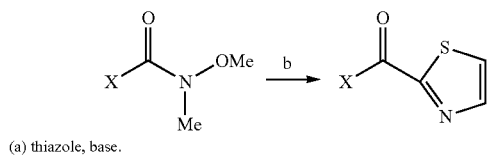

(a) thiazole, base.

There are still further ways of developing a 2-oxo thiazole ring carrying a substituent. The ring itself can be generated from a thioamide as described in scheme 3.

Scheme 3.

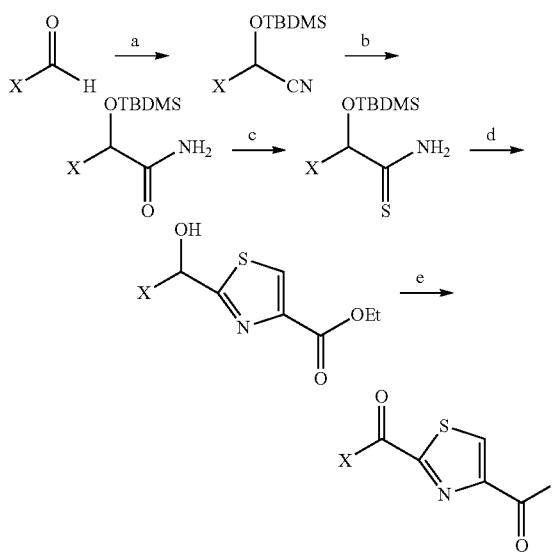

(a) TBDMSCH, KCN; (b) $H_2O_2$, $Bu_4NHSO_4$; (c) Lawesson's reagent;
(d) $BrCH_2COCOOEt$; (e) Dess Martin periodinane.

The formed compound can react with thiazole as described above. Variations of the substituents on the heterocyclic rings and manipulation of the side chain binding the carbonyl can be achieved using all manner of synthetic techniques which the skilled man will know. Guidance is offered in the examples as to how to make a wide variety of compounds and the principles described can be extended to the compounds encompassed by the claims. WO2011/039365 also offers synthetic pathways to follow.

Chronic Inflammatory Disorders

The compounds of the invention may be used in the prevention or treatment of chronic inflammatory disorders, in particular those associated with phospholipase inhibition.

Preferably, any compound of the invention will achieve at least 75%, such as at least 90% inhibition against group IVa $PLA_2$.

Preferably, compounds of the invention inhibit group IVa $cPLA_2$ at a low μM range such as 5 μM or less, preferably 4 μM or less.

It is further preferred that the compounds of formula (I) of the invention show greater inhibition of group IVa $cPLA_2$ than $iPLA_2$ or $sPLA_2$ according to published assays for these enzymes (see, for example, Yang, H et al. (1999) *Anal. Biochem.* 269: 278). Ideally, the compounds of the invention show limited or no inhibition of $iPLA_2$ or $sPLA_2$ and they are therefore highly specific for the group IVa $cPLA_2$ enzyme.

Specific diseases of interest are glomerulonephritis, inflammatory dermatoses such as psoriasis and rheumatoid arthritis.

Further conditions of interest include other inflammatory dermatoses such as atopic dermatitis, allergic contact dermatitis, seborrheic dermatitis, *pityriasis rosea*, lichen planus and drug eruptions.

Furthermore the compounds of the invention may have use in the treatment of other types of arthritis and dermatoses, inflammatory CNS diseases, multiple sclerosis, chronic obstructive pulmonary disease, chronic lung inflammatory conditions, inflammatory bowel disease such as ulcerative colitis and crohns disease, and cardiovascular disease. Furthermore, the compounds of the invention may have use in the treatment of juvenile arthritis, Crohn's colitis, psoriatic arthritis and ankylosing spondylitis.

Thus viewed from a further aspect the invention provides for the management (typically an alleviation of symptoms), prevention or treatment of any of the conditions listed above using the compounds of the invention.

In one embodiment, the prevention, treatment, or alleviation of symptoms of a chronic inflammatory condition such as those mentioned above can be achieved by administering at least one compound according to the invention (e.g., one, two or three of such compounds) to a subject as the sole active agent. Alternatively, the chronic inflammatory condition can be prevented, treated or symptoms alleviated along with at least one suitable anti-inflammatory drug (e.g., one, two or three of such drugs). Non-limiting examples of such drugs include certain steroids (e.g., corticosteroids), non-steroidal anti-inflammatory drugs (NSAIDs) such as aspirin, ibuprofen and naproxen, and analgesics such as paracetamol, acetaminophen and the like; as well as ImSAIDs.

It will be appreciated that when the indication to be treated is rheumatoid arthritis or a related disorder, the subject may be receiving or will receive a disease modifying antirheumatic drug (known as DMARD) such as methotrexate, leflunomide, hydroxychloroquine, sulfasalazine, and the like. In one embodiment, the DMARD can be administered along with at least one compound of the invention such as one, two or three of such compounds. In another embodiment, the subject can receive in addition to the DMARD a suitable biologic such as those mentioned below along with at least one compound of the invention such as one, two or three of such compounds. When a subject starts using a particular biologic agent, they will often also remain on their current dose of nonsteroidal anti-inflammatory (NSAID) and/or corticosteroid (i.e., prednisone) medicines.

It will be appreciated that therapeutic methods according to the invention are flexible and can be practiced in several ways to achieved a desired outcome. Thus in one embodiment, the method includes administering a compound having Formula I to a subject (e.g., using an oral, i.v, i.p or other route) followed by administration of an anti-inflammatory drug as described herein. Use of a suitable biologic (e.g. an antibody therapeutic as provided herein) may also be indicated. Alternatively, the method can be practiced by administering the anti-inflammatory drug first followed by administration of the compound of the invention. Choice of a particular methodology and administration route will be guided by understood parameters such as the chronic inflammatory disorder to be treated, age and sex of the subject, etc.

Hyperproliferative Disorders

In another aspect, the invention provides compounds of the invention for use in the management, treatment or prevention of any condition or clinical situation where it is desirable (or where it may be of benefit) to prevent or inhibit the growth of cells. Examples include tumors, cancers, neoplastic tissues, and other premaligant and noneoplastic hyperproliferative disorders, all of which together are referred to herein as hyperproliferative or hyperplastic disorders.

The term "inhibit" is used broadly to include any reduction or decrease in cell growth as well as the prevention or abolition of cell growth. "Inhibition" thus includes the reduction or prevention of cell growth. This may be determined by any appropriate or convenient means, such as determining or assessing cell number, size (e.g size of tissue in which the cells are contained), cell viability and/or cell death etc., as may be determined by techniques well known in the art.

"Growth" of cells as referred to herein is also used broadly to include any aspect of cell growth, including in particular the proliferation of cells.

The compounds of the invention may thus be used in the treatment of any condition (used broadly herein to include any disorder or any clinical situation) which is responsive to reduction of cell growth (particularly cell proliferation). The compounds accordingly find utility in any therapy (or treatment) which targets cell growth (or proliferation). In other words, the compounds may be used in any therapeutic application in which it is desirable or advantageous to inhibit cell proliferation.

A treatment may include any clinical step or intervention which contributes to, or is a part of, a treatment programme or regimen. A prophylactic treatment may include delaying, limiting, reducing or preventing the condition or the onset of the condition, or one or more symptoms thereof, for example relative to the condition or symptom prior to the prophylactic treatment. Prophylaxis thus explicitly includes both absolute prevention of occurrence or development of the condition, or symptom thereof, and any delay in the onset or development of the condition or symptom, or reduction or limitation on the development or progression of the condition or symptom. Treatment according to the invention thus includes killing, inhibiting or slowing the growth of cells, or the increase in size of a body or population of cells (e.g in a tissue, tumour or growth), reducing cell number or preventing spread of cells (e.g to another anatomic site), reducing the size of a cell growth etc. The term "treatment" does not imply cure or complete abolition or elimination of cell growth, or a growth of cells.

Since the therapeutic applications and utilities of the present invention may generally involve inhibiting cell proliferation, nearly any proliferating cell may be targeted in the therapies and utilities disclosed and encompassed herein. Such proliferating cells may include healthy or diseased cells and cells of any tissue in which proliferation occurs. For example, such cells may include in particular neoplastic cells, including both malignant and non-malignant neoplastic cells and cells of the immune system (immune cells), cells of the haematopoietic system generally, or skin cells.

The compounds of the invention can be employed to treat one or a combination of hyperproliferative disorders as the sole active agent or in combination with one or more other agents. In one embodiment, disorders or conditions involving abnormal or unwanted cell growth may be treated with known agents including known cytotoxic and/or cytostatic agents including chemotherapeutic agents. Accordingly, as alternatively stated above, the compounds of the invention may be used in any method of treatment which involves (or includes) the use of such cytotoxic and/or cytostatic agents. This may include the treatment of any condition responsive to a cytotoxic and/or cytostatic agent or any condition which may be treated with or which requires the use of such agent(s).

The treatment of hyperproliferative disorders represents an aspect of particular interest. The term "hyperproliferative disorder" is used broadly herein to include any disorder or condition which involves increased, undesired or unwanted proliferation of cells. Thus included are not only conditions in which proliferation of cells is increased, for example relative to normal or healthy cells, or cells in the absence of the condition in question (e.g. compared or relative to a healthy or control subject, or compared or relative to cells taken from healthy or unaffected tissue in the same subject), but also conditions in which cell proliferation is not increased (or not greatly or significantly increased) over normal, but in which the proliferation which occurs is unwanted or undesired, whether generally or in a particular context. This may include for example an unwanted or undesired proliferation of cells which may occur in a "normal" response.

A hyperproliferative disorder of particular interest involves the proliferation of cells which have the capacity for autonomous growth i.e. cells which exist and reproduce independently of normal regulatory mechanisms. A hyperproliferative disorder may therefore be a neoplastic disorder, and as noted above, this may be a pre-malignant, malignant, non-malignant or non-neoplastic disorder. Examples of pre-malignant or non-neoplastic or non-malignant hyperproliferative disorders include myelodysplastic disorders, cervical carcinoma-in-situ, familial intestinal polyposes (e.g. Gardner syndrome), oral leukoplasias, histiocytoses, keloids, hemangiomas, hyperproliferative arterial stenosis, inflammatory arthritis, hyperkeratoses, and papulosquamous eruptions, including arthritis. Also included are viral-induced hyperproliferative diseases such as warts and EBV-induced disease (e.g. infectious mononucleosis), scar formation and the like.

The hyperproliferative disorder may thus be any hyperproliferative disorder, for example selected from neoplastic disorders such as cancer (benign or metastatic). Cancer represents a hyperproliferative disorder of particular interest, and all types of cancers, including e.g. solid tumours and haematological cancers are included. Representative types of cancer include cervical cancer, uterine cancer, ovarian cancer, pancreatic cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, pancreatic cancer, endometrial cancer, plasmacytoma, lymphomas, retinoblastoma, Wilm's tumor, Ewing sarcoma, melanoma and other skin cancers.

Mention may be made also of sinus tumours, urethral and genito-urinary cancers, oesophageal cancer, myeloma, endocrine cancers, osteosarcoma, angiosarcoma, and fibrosarcoma, and any tumour of the peripheral or central nervous systems, malignant or benign, including gliomas and neuroblastomas.

In embodiments in which the hyperproliferative disorder is a cancer, the invention also features methods of treating a subject (e.g. a human that has or is suspected of having cancer) in which the method includes treating the subject with at least one compound of the invention, preferably one, two or three of such compounds alone or along with an effective amount of one or more agents having cytotoxic or cytostatic activity such as a chemotherapeutic agent (e.g., one, two or three of such agents). Illustrative chemotherapeutic agents are "small molecules" selected from the group consisting of abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

Other suitable chemotherapeutic agents for use with the invention include biologics such as immune molecules that exhibit a cytotoxic or cytostatic activity against a targeted cell or tissue. More specific examples include antibodies and antigen-binding fragments thereof, namely monoclonal, polyclonal, chimeric and humanized antibodies. Non-limiting examples include the following therapeutic antibodies that have been approved for human use for several medical indications: Abciximab (ReoPro), Adalimumab (Humira), Alemtuzumab (Campath), Basiliximab (Simulect), Belimumab (Benlysta), Bevacizumab (Avastin), Brentuximab vedotin (Adcetris), Canakinumab (Ilaris) Cetuximab (Erbitux), Certolizumab pegol[19] (Cimzia), Daclizumab (Zenapax), Denosumab (Prolia, Xgeva), Eculizumab (Soliris), Efalizumab (Raptiva), Gemtuzumab (Mylotarg), Golimumab (Simponi), Ibritumomab tiuxetan (Zevalin), Infliximab (Remicade), Ipilimumab (MDX-101) (Yervoy), Muromonab-CD3, (Orthoclone OKT3), Natalizumab (Tysabri), Ofatumumab (Arzerra), Omalizumab (Xolair), Palivizumab (Synagis), Panitumumab (Vectibix), Ranibizumab (Lucentis), Rituximab (Rituxan, Mabthera) Tocilizumab (or Atlizumab) (Actemra and RoActemra), Tositumomab (Bexxar) and Trastuzumab (Herceptin).

Also included within the scope of suitable biologics for use with the invention are certain antibody-small molecule conjugates such as TDM1 (conjugate of trastuzumab and doxorubicin).

In embodiments in which the hyperproliferative disorder is cancer and particularly a cancer of the breast, the chemotherapeutic drug may be selected from the following: Abitrexate (Methotrexate), Abraxane (Paclitaxel Albumin-stabilized Nanoparticle Formulation) Ado-Trastuzumab Emtansine, Adriamycin PFS (Doxorubicin Hydrochloride), Adriamycin RDF (Doxorubicin Hydrochloride), Adrucil (Fluorouracil), Afinitor (Everolimus), Anastrozole, Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Efudex (Fluorouracil), Ellence (Epirubicin Hydrochloride), Epirubicin Hydrochloride, Everolimus, Exemestane, Fareston (Toremifene), Faslodex (Fulvestrant), Femara (Letrozole), Fluoroplex (Fluorouracil), Fluorouracil, Folex (Methotrexate), Folex PFS (Methotrexate), Fulvestrant, Gemcitabine Hydrochloride, Gemzar (Gemcitabine Hydrochloride), Herceptin (Trastuzumab), Ixabepilone, Ixempra (Ixabepilone), Lapatinib Ditosylate, Letrozole, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation, Perjeta (Pertuzumab), Pertuzumab, Tamoxifen Citrate, Taxol (Paclitaxel), Taxotere (Docetaxel), Trastuzumab, Toremifene, Tykerb (Lapatinib Ditosylate), and Xeloda (Capecitabine)

In another aspect, the invention features methods of treating a subject (e.g. a human) having or suspected of having a hyperproliferative disorder such as cancer, involving administering to the subject an effective amount of a compound according to Formula I or II either as a sole agent or along with an effective amount of one or more chemotherapeutic agents described above (e.g., one, two or three of such agents). An illustrative treatment regimen involves treating, preventing or minimizing tumor progression or metastasis in a subject having a neoplasia, where the neoplastic cell is a cancer cell or is present in a tumor.

In another aspect, the invention features a method of treating, preventing or minimizing tumor progression or metastasis in a subject where the tumor is breast cancer, melanoma, glioblastomas, colon cancer, non-small cell lung cancer, or lymphomas, involving administering to the subject an effective amount of at least one compound of the invention (e.g., one, two or three of such compounds) alone or along with one or more other chemotherapeutic agents as described herein (e.g, one or two of such agents).

In a particularly preferred embodiment, the invention relates to a method for preventing or treating breast cancer in a patient, the method comprising the steps of administering to the patient an effective amount of at least one chemotherapeutic agent; and administering an effective amount of at least one compound of the invention.

It is further preferred if a chemotherapeutic agent is administered to the patient before the administration of the compound of the invention, such as one or more of paclitaxel, doxorubicin, cyclophosphamide and cisplatin.

The method may also comprise the administration of one or more of trastuzumab (Herceptin), trastuzumab-doxorubicin conjugate (TDM1) and pertuzumab (Perjeta).

It will be appreciated that therapeutic methods according to the invention are flexible and can be practiced in several ways to achieved a desired outcome for the subject. Thus in one embodiment, the method includes administering a compound having Formula I or II to a subject (e.g., using an oral, i.v, i.p or other route) followed by administration of at least one chemotherapeutic agent as described herein (e.g., one, two or three of such agents). Alternatively, the method can be practiced by administering the chemotherapeutic agent first followed by administration of the compound of the invention. Choice of a particular methodology and administration route will be guided by understood parameters such as the hyperproliferative disorder to be treated, age and sex of the subject, etc.

The method of the invention may also comprise the treatment of chronic inflammatory disorders associated a diabetic condition in a patient, particularly diabetes mellitus, such as diabetic nephropathy and diabetic retinopathy.

Subjects to be treated by the methods of the present invention include both human subjects (patients) and animal subjects for veterinary purposes. Animal subjects are generally mammalian subjects such as horses, dogs, cats, cows, rabbits, sheep and the like.

Screen

Suitable compounds for use with the present methods for treating, preventing or alleviating symptoms a hyperproliferative disorder can be selected by one or a combination of different strategies which are intended to detect and preferably quantify changes in cell proliferation when contacted by one or more invention compounds. Non-limiting examples of such screens are provided below:

a. NCI60 Screen:

In one approach, a compound of the invention is tested for efficacy in the NCI60 human humor cell line anticancer drug screen reported by Shoemaker, R. H (2006) *Nat. Reviews Cancer* 6, 813. Briefly, the NCI60 screen is a two-stage process, beginning with the evaluation of all compounds against 60 cell lines at a single dose of 10 µM. Compounds giving a growth inhibition of 50% (GI50) is calculated from [(Ti-Tz)/(C-Tz)]×100=50, which is the compound concentration resulting in a 50% reduction in the net protein increase (as measured by SRB staining) in control cells during the incubation. Preferred compounds of formula (I) or (II) of the invention have a GI50 of about 1-5 µM in the NCI60 screen, more preferably about 0.01-0.1 µM or less with respect to at least one of the cell lines in the NCI60 screen.

See also Alley, M. C., et al. Cancer Research 48: 589-601, 1988; Grever, M. R., et al. The National Cancer Institute: Cancer Drug Discovery and Development Program. Seminars in Oncology, Vol. 19, No. 6, pp 622-638, 1992; and Boyd, M. R., and Paull, K. D. Some Practical Considerations and Applications of the National Cancer Institute In Vitro Anticancer Drug Discovery Screen. Drug Development Research 34: 91-109, 1995.

b. Screen Based on Clin Cancer Res. 2008 Dec. 15; 14(24):8070-9.

Patel M I, Singh J, Niknami M, Kurek C, Yao M, Lu S, Maclean F, King N J, Gelb M H, Scott K F, Russell P J, Boulas J, Dong Q.

In another approach the expression of cPLA2-alpha can be determined in prostate cancer cells by reverse transcription-PCR, Western blot, and immunocytochemistry. Growth inhibition, apoptosis, and cPLA2-alpha activity can be determined after inhibition with cPLA2-alpha small interfering RNA or inhibitor (Wyeth-1). Cytosolic PLA2-alpha inhibitor or vehicle can also be administered to prostate cancer xenograft mouse models. Finally, the expression of phosphorylated cPLA2-alpha can be determined by immunohistochemistry in human normal, androgen-sensitive and androgen-insensitive prostate cancer specimens.

Formulation

Irrespective of their intended use, the compounds of the invention are preferably formulated as pharmaceutically acceptable compositions. The phrase "pharmaceutically acceptable", as used in connection with compositions of the invention, refers to molecular entities and other ingredients of such compositions that are physiologically tolerable and do not typically produce untoward reactions when administered to a mammal (e.g. human). Preferably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18th Edition, incorporated by reference. Particularly preferred for the present invention are carriers suitable for immediate-release, i.e., release of most or all of the active ingredient over a short period of time, such as 60 minutes or less, and make rapid absorption of the drug possible.

Any compound of the invention can be administered in salt, solvate, prodrug or ester form, especially salt form. Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of the invention and the resulting mixture evaporated to dryness (lyophilised) to obtain the acid addition salt as a solid. Alternatively, a compound of the invention may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The salts of the compound of the invention may form solvates (e.g. hydrates) and the invention also includes all such solvates.

The term "prodrug" as used herein means a compound which is converted within the body, e.g. by hydrolysis in the blood, into its active form that has medical effects.

The compounds of the invention are proposed for use in the treatment of, inter alia, chronic inflammatory disorders and cancer. The compounds of the invention are also proposed for use in the treatment of, inter alia, cancer. By treating or treatment is meant at least one of:

(i). preventing or delaying the appearance of clinical symptoms of the disease developing in a mammal;

(ii). inhibiting the disease i.e. arresting, reducing or delaying the development of the disease or a relapse thereof or at least one clinical or subclinical symptom thereof, or (iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs.

The word "treatment" is also used herein to cover prophylactic treatment, i.e. treating subjects who are at risk of developing a disease in question.

The compounds can be used on any animal subject, in particular a mammal and more particularly to a human or an animal serving as a model for a disease (e.g. mouse, monkey, etc.).

An "effective amount" means the amount of a compound that, when administered to an animal for treating a state, disorder or condition, is sufficient to effect such treatment. The "effective amount" will vary depending on the compound, the disease and its severity and the age, weight, physical condition and responsiveness of the subject to be treated and will be ultimately at the discretion of the attendant doctor.

While it is possible that, for use in the methods of the invention, a compound may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients.

There may be different composition/formulation requirements depending on the different delivery systems. Likewise, if the composition comprises more than one active component, then those components may be administered by the same or different routes.

The pharmaceutical formulations of the present invention can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

The compounds of the invention can be administered for immediate-, delayed-, modified-, sustained-, pulsed- or controlled-release applications.

In one aspect, oral compositions are slow, delayed or positioned release (e.g., enteric especially colonic release) tablets or capsules. This release profile can be achieved without limitation by use of a coating resistant to conditions within the stomach but releasing the contents in the colon or other portion of the GI tract wherein a lesion or inflammation site has been identified or a delayed release can be achieved by a coating that is simply slow to disintegrate or the two (delayed and positioned release) profiles can be combined in a single formulation by choice of one or more appropriate coatings and other excipients. Such formulations constitute a further feature of the present invention.

Pharmaceutical compositions can be prepared by mixing a therapeutically effective amount of the active substance with a pharmaceutically acceptable carrier that can have different forms, depending on the way of administration. Typically composition components include one or more of binders, fillers, lubricants, odorants, dyes, sweeteners, surfactants, preservatives, stabilizers and antioxidants.

The pharmaceutical compositions of the invention may contain from 0.01 to 99% weight—per volume of the active material. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is within the scope of the invention for a compound as described herein to be administered in combination with another pharmaceutical, e.g. another drug with known efficacy against the disease in question. The compounds of the invention may therefore be used in combination therapy.

The chemistry described in the following schemes is used to manufacture the compounds described in the tables which follow. The starting materials in each scheme are readily available compounds. In general, molar equivalents of each reactant are employed.

The invention will now be further described with reference to the following non limiting examples.

Examples

The following general reactions can be used to manufacture the compounds of the invention:

Linear sequences starting from 4-hydroxybenzaldehydes may be developed.

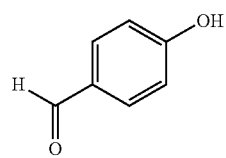

Alternatively, it is possible to use a convergent approach where two halves of equal sizes are joined in the last step. This is advantageous for several reasons; one half is kept constant, whereas the other half provides several opportunities for easy introduction of variations. Furthermore, the total number of steps is kept low.

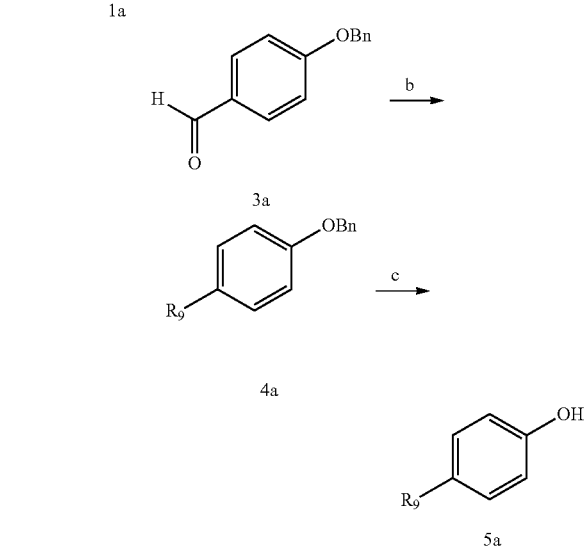

Scheme 4.

Reagents and conditions: a) base, BnBr; b) heptylphosphonium bromide, BuLi, THF; c) H$_2$ (g), Pd/C.

Scheme 4 is applicable for compounds such as example 3 below and comprises mainly standard reactions. After introduction of a protecting group in the first step, Wittig coupling with an alkylphosphonium salt of suitable length provides compounds 4. By protecting the phenol as benzyl ether, reduction of the double bond and deprotection can be obtained simultaneously, giving substituted octylphenols (5). If another protecting group is selected, the double bond in 4 might be possible to preserve in the final product, providing another opportunity for variation.

For the second fragment, we suggest a route starting with 2,4-dibromothiazole (6, commercially available). For the first two lithiation steps, there are opportunities for rearrangements. The TMS derivative 7 we suggest is less prone to rearrangement.

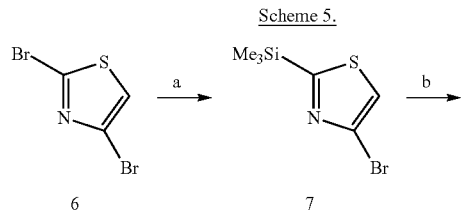

Scheme 5.

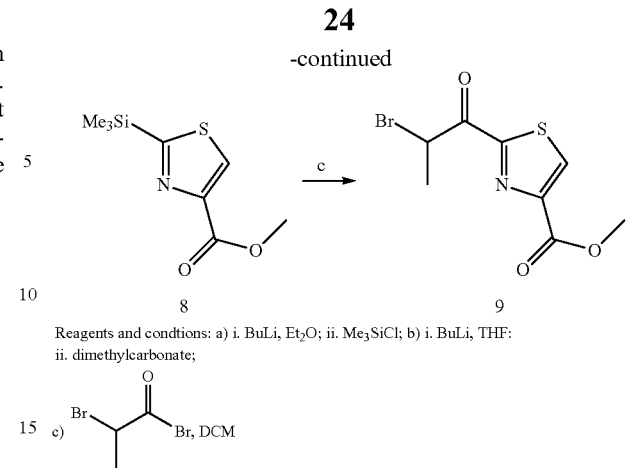

Reagents and conditions: a) i. BuLi, Et$_2$O; ii. Me$_3$SiCl; b) i. BuLi, THF; ii. dimethylcarbonate;

c) Br—CH(CH$_3$)—C(O)—Br, DCM

The last step in Scheme 5 to fragment 9 is well established (Dondoni et al, J. Am. Chem. Soc. 116 (1994) 3324).

The two fragments 5 and 9 are finally joined by a standard Williamson ether preparation, Scheme 6.

Scheme 6.

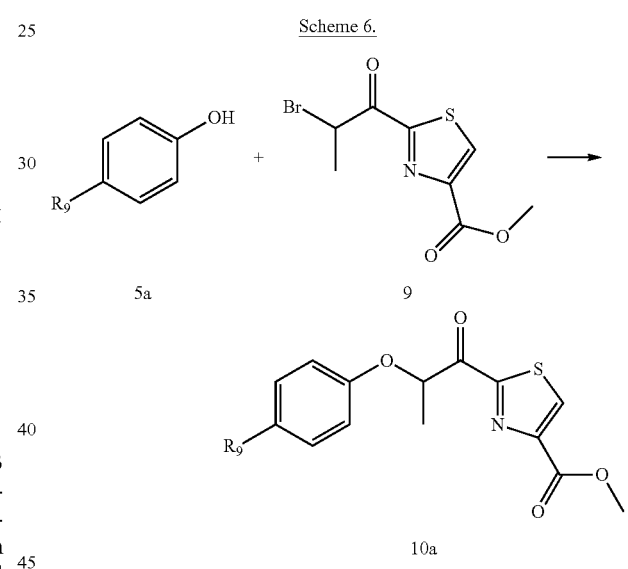

Reagents and conditions; K$_2$CO$_3$, acetone.

The synthesis of thiazole derivatives 32a,b and 37a-c is presented in Schemes 6 and 7. Phenols 28a,b and 33a,b were treated with ethyl bromoacetate. Esters 29a,b were hydrolyzed and converted to their corresponding Weinreb amides. Treatment of 31a,b with lithium thiazole led to the target derivatives 32a,b. Oxothiazoles 37a-c were prepared by another procedure. Alcohols 35a,b were oxidized to aldehydes and treated with lithium thiazole or benzothiazole. Compounds 36a-c were then oxidized to the final compounds.

Substituted thiazoles 43a-c and 47 (Compound A) were synthesized as illustrated in Schemes 12 and 13. The key-step in this synthesis was the formation of the substituted heterocyclic ring. Alcohols 35b and 38 were oxidized to aldehydes and directly treated with TBDMSCN. Compounds 39a,b were converted into amides and subsequently into thioamides by reaction with Lawesson's reagent. Treatment of 41a,b with ethyl 4-chloroacetoacetate or ethyl bromopyruvate in the presence of conc. H$_2$SO$_4$ led to heterocyclic derivatives 42a-c which were then oxidized to the final compounds 43a-c. Following another method for the formation of the heterocyclic ring, condensation of cysteine methyl ester with nitrile 39a afforded a diastereomeric mixture of thiazoline 44, which was transformed into thiazole 45 using BrCCl₃ and DBU. Subsequent removal of the silyl group and Dess-Martin oxidation led to the oxothiazole 47.

Scheme 6:

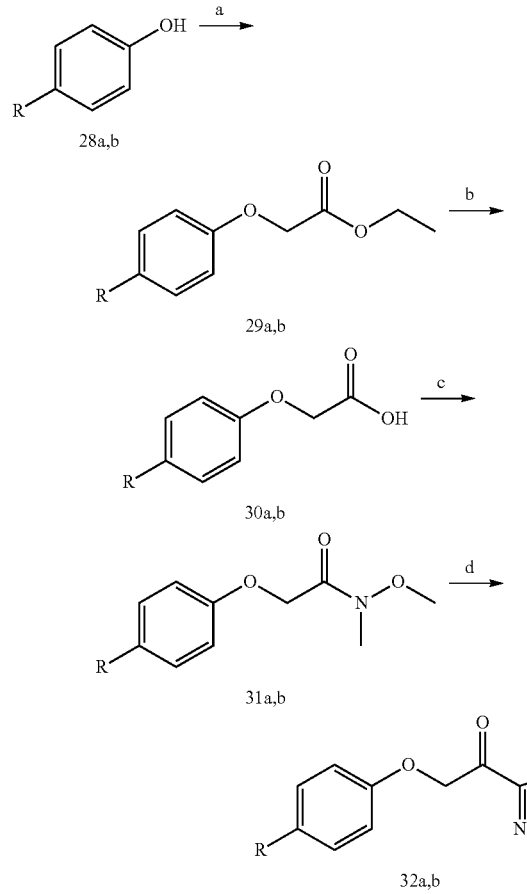

| 28-32 | R |
|---|---|
| a | OPhOMe |
| b | OPhCF3 |

Scheme 6 Reagents and conditions:
a) BrCH₂COOEt, K₂CO₃, acetone;
b) 1N aq. NaOH, EtOH;
c) HCl•NH(OMe)Me, NMM, DMAP, WSCI•HCl, CH₂Cl₂;
d) thiazole, n-BuLi, Et₂O.

Scheme 7:

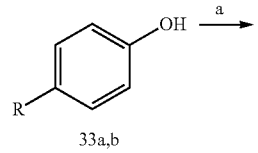

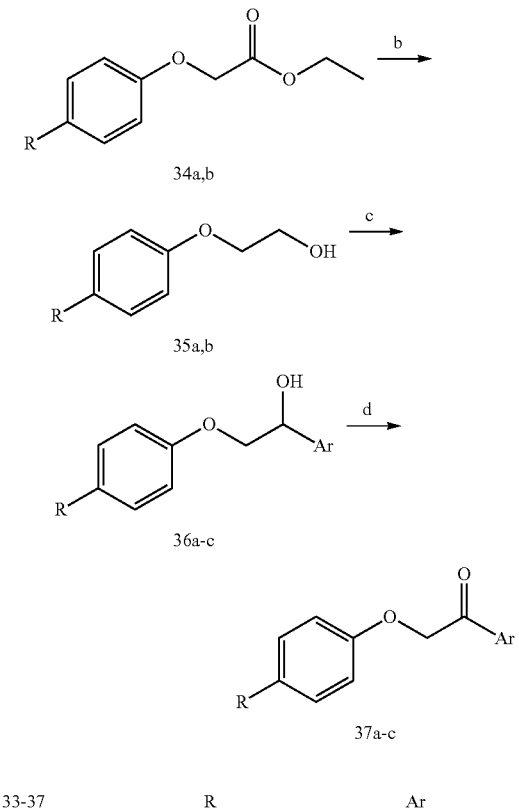

| 33-37 | R | Ar |
|---|---|---|
| a | OC₆H₅ | thiazole |
| b | OCH2C6H5 | thiazole |
| c | OPh—F | thiazole |

Scheme 7 reagents and conditions:
a) BrCH₂COOEt, K₂CO₃, acetone;
b) DIBALH, Et₂O;
c) i. NaOCl, TEMPO, NaBr, NaHCO₃, EtOAc/PhCH₃/H₂O 3:3:0.5, −5° C.; ii. thiazole or benzothiazole, n-BuLi, Et₂O;
d) Dess-Martin periodinane, CH₂Cl₂.

Scheme 8:

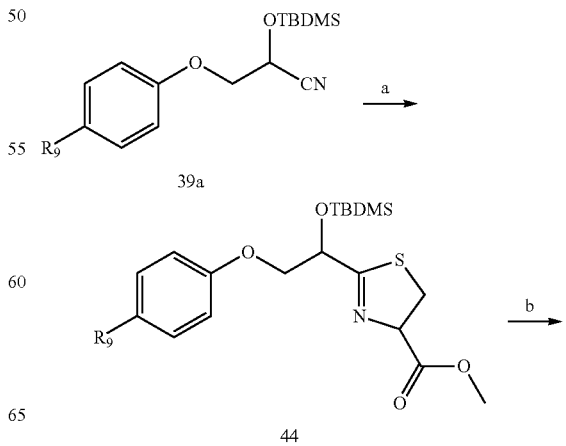

27
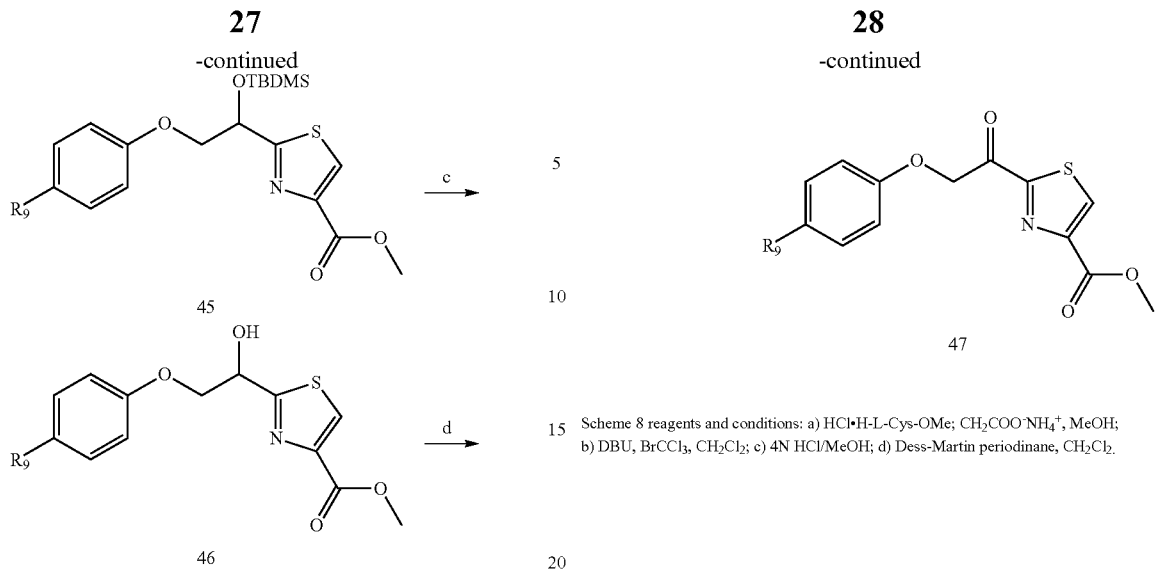
45
46
28
-continued
47
Scheme 8 reagents and conditions: a) HCl•H-L-Cys-OMe; CH₂COO⁻NH₄⁺, MeOH; b) DBU, BrCCl₃, CH₂Cl₂; c) 4N HCl/MeOH; d) Dess-Martin periodinane, CH₂Cl₂.
The following compounds can then be prepared:
| Compound | Structure |
|---|---|
| 1 | 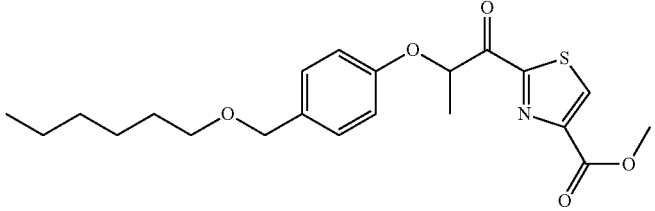 [SMILES: CCCCCCOCc1ccc(OC(C)C(=O)c2nc(C(=O)OC)cs2)cc1] |
| 2 | 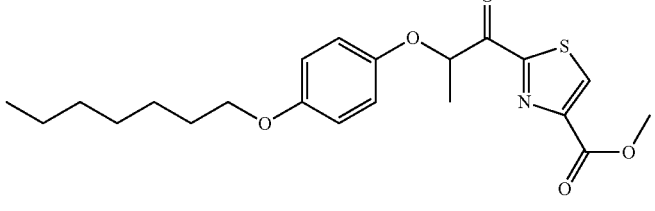 |
| 3 | 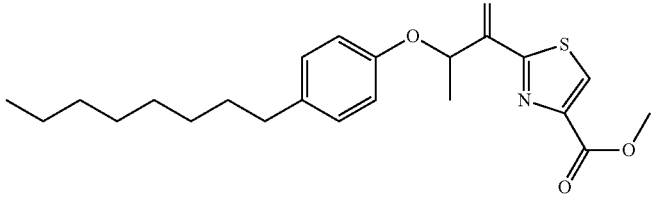 |
| 4 | 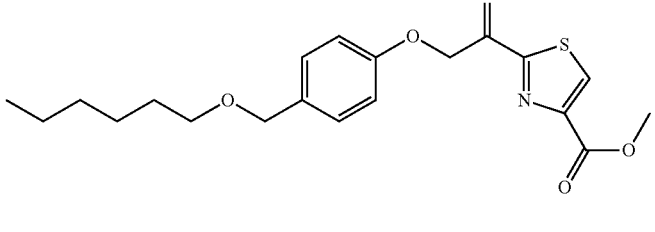 |

-continued

| Compound | Structure |
|---|---|
| 5 | (methyl 2-(2-(4-phenoxyphenoxy)acetyl)thiazole-4-carboxylate) |
| 6 | (methyl 2-(2-(4-(4-fluorophenoxy)phenoxy)acetyl)thiazole-4-carboxylate) |
| 7 | (methyl 2-(2-(4-(4-(trifluoromethyl)phenoxy)phenoxy)acetyl)thiazole-4-carboxylate) |
| 8 | (methyl 2-(2-(4-(4-methoxyphenoxy)phenoxy)acetyl)thiazole-4-carboxylate) |
| 9 | (methyl 2-(2-(4-((4-methoxybenzyl)oxy)phenoxy)acetyl)thiazole-4-carboxylate) |
| 10 | (methyl 2-(2-(4-(phenethylthio)phenoxy)acetyl)thiazole-4-carboxylate) |

-continued

| Compound | Structure |
|---|---|
| 11 | *(structure image)* |
| 12 | *(structure image)* |
| 13 | *(structure image)* |
| 14 | *(structure image)* |
| 15 | *(structure image)* |
| 16 | *(structure image)* |
| 17 | *(structure image)* |

Example Protocols

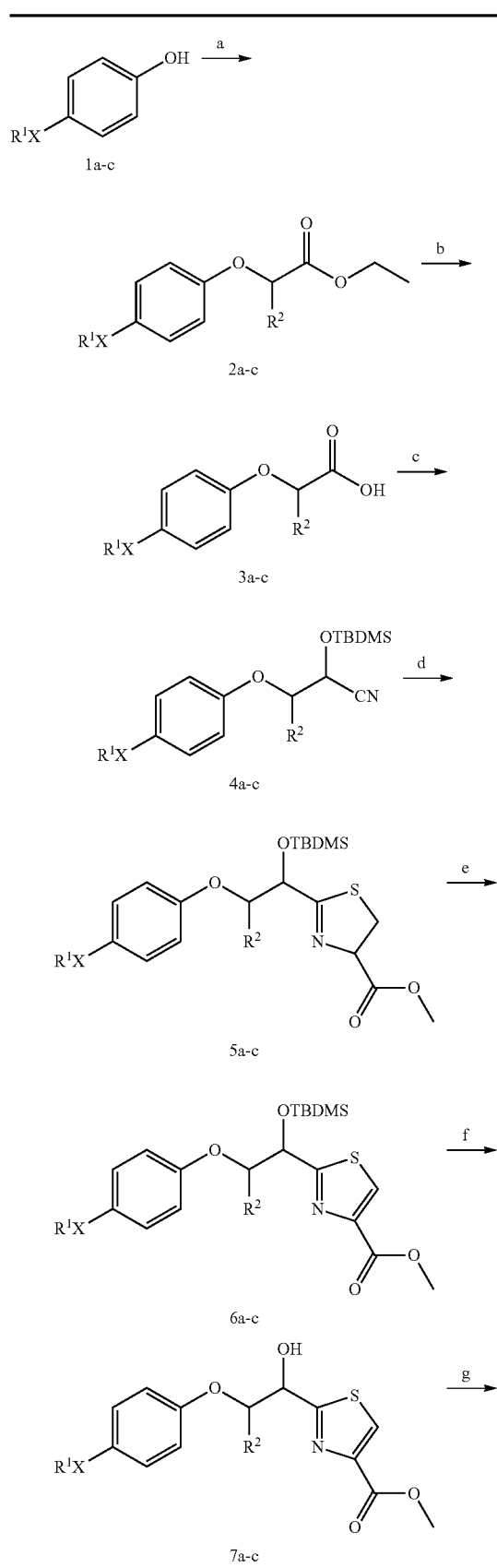

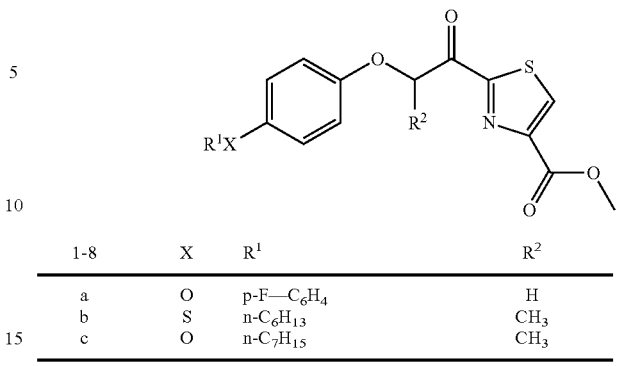

| 1-8 | X | $R^1$ | $R^2$ |
|---|---|---|---|
| a | O | p-F—$C_6H_4$ | H |
| b | S | n-$C_6H_{13}$ | $CH_3$ |
| c | O | n-$C_7H_{15}$ | $CH_3$ |

Scheme 9.
Reagents and conditions:
(a) $BrCH_2COOEt$ or $BrCH(CH_3)COOEt$, $K_2CO_3$, acetone;
(b) DIBALH, $Et_2O$;
(c) i. NaOCl, TEMPO, NaBr, $NaHCO_3$, $EtOAc/PhCH_3/H_2O$ 3:3:0.5, −5° C.; ii. TBDM-SCN, 18-crown-6, KCN, $CH_2Cl_2$;
(d) HCl•H-L-Cys-OMe, $CH_3COO^-NH_4^+$, MeOH;
(e) DBU, $BrCCl_3$, $CH_2Cl_2$;
(f) 4N HCl/MeOH;
(g) Dess-Martin periodinane, $CH_2Cl_2$.

Experimental Section

General Method for the Synthesis of Acetates 2a-c.

To a stirred solution of phenols 1a-c (1.0 mmol) in acetone (10 mL), $K_2CO_3$ (3 mmol, 415 mg) and ethyl bromoacetate or ethyl 2-bromopropionate (1.1 mmol) were added, and the reaction mixture was refluxed for 5 h. Subsequently, the mixture was filtrated over Celite, and the organic solvent was evaporated under reduced pressure. The residue was purified by column chromatography [EtOAc-petroleum ether (bp 40-60° C.), 1:9].

Ethyl 2-(4-(4-fluorophenoxy)phenoxy)acetate (2a)

Yield 94%; White oil; $^1$H NMR (200 MHz, $CDCl_3$): δ 7.15-6.78 (m, 8H), 4.61 (s, 2H), 4.29 (q, J=7.2 Hz, 2H), 1.31 (t, J=7.2 Hz, 3H).

Ethyl 2-(4-(hexylthio)phenoxy)propanoate (2b)

Yield 91%; White oil; $^1$H NMR (200 MHz, $CDCl_3$): δ 7.24 (d, J=9.0 Hz, 2H), 6.75 (d, J=9.0 Hz, 2H), 4.66 (q, J=6.8 Hz, 1H), 4.15 (q, J=7.2 Hz, 2H), 2.75 (t, J=7.0 Hz, 2H), 1.62-1.42 (m, 5H), 1.41-1.05 (m, 9H), 0.82 (t, J=7.0 Hz, 3H); $^{13}$C NMR (50 MHz, $CDCl_3$): δ 171.7, 156.3, 132.1, 127.9, 115.4, 72.4, 61.0, 35.1, 31.1, 29.0, 28.1, 22.3, 18.3, 13.9, 13.8.

Ethyl 2-(4-(heptyloxy)phenoxy)propanoate (2c)

Yield 97%; White oil; $^1$H NMR (200 MHz, $CDCl_3$): δ 6.84-6.65 (m, 4H), 4.62 (q, J=6.8 Hz, 1H), 4.17 (q, J=7.2 Hz, 2H), 3.85 (t, J=6.6 Hz, 2H), 1.80-1.61 (m, 2H), 1.55 (d, J=6.8 Hz, 3H), 1.46-1.06 (m, 11H), 0.87 (t, J=6.6 Hz, 3H); $^{13}$C NMR (50 MHz, $CDCl_3$): δ 172.3, 153.8, 151.4, 116.2, 115.1, 73.4, 68.2, 61.0, 31.6, 29.2, 28.9, 25.9, 22.5, 18.4, 13.9.

General Method for the Synthesis of Alcohols 3a-c.

To a stirred solution of esters 2a-c (1 mmol) in dry $Et_2O$ (10 mL) was added DIBALH (2.5 mL, 2.5 mmol, 1.0 M in hexane) at 0° C. under Ar atmosphere and the reaction mixture was stirred for 2 h at room temperature. Water was then added (5 mL), the mixture was stirred for 30 more minutes and filtrated over Celite. The organic solvent was evaporated under reduced pressure and the residue was purified by column chromatography [EtOAc-petroleum ether (bp 40-60° C.), 3:7].

2-(4-(4-Fluorophenoxy)phenoxy)ethanol (3a)

Yield 89%; White solid; $^1$H NMR (200 MHz, CDCl$_3$): δ 7.07-6.76 (m, 8H), 4.10-3.84 (m, 4H), 2.94 (br s, 1H); $^{13}$C NMR (50 MHz, CDCl$_3$): δ 160.6, 155.8, 154.6, 153.9, 150.8, 120.0, 119.1, 116.2, 115.5, 69.6, 61.1.

2-(4-(Hexylthio)phenoxy)propan-1-ol (3b)

Yield 85%; White oil; $^1$H NMR (200 MHz, CDCl$_3$): δ 7.28 (d, J=8.8 Hz, 2H), 6.75 (d, J=8.8 Hz, 2H), 4.51-4.32 (m, 1H), 3.74-3.58 (m, 2H), 2.79 (t, J=7.0 Hz, 2H), 2.68 (s, 1H), 1.66-1.46 (m, 2H), 1.45-1.12 (m, 9H), 0.85 (t, J=6.6 Hz, 3H); $^{13}$C NMR (50 MHz, CDCl$_3$): δ 156.5, 132.5, 127.4, 116.4, 74.8, 65.9, 35.4, 31.2, 29.1, 28.3, 22.4, 15.6, 13.9.

2-(4-(Heptyloxy)phenoxy)propan-1-ol (3c)

Yield 92%; White solid; $^1$H NMR (200 MHz, CDCl$_3$): δ 6.94-6.74 (m, 4H), 4.43-4.24 (m, 1H), 3.90 (t, J=6.6 Hz, 2H), 3.75-3.60 (m, 2H), 2.77 (br s, 1H), 1.87-1.65 (m, 2H), 1.57-1.25 (m, 8H), 1.22 (d, J=6.2 Hz, 3H), 0.91 (t, J=6.6 Hz, 3H); $^{13}$C NMR (50 MHz, CDCl$_3$): δ 153.7, 151.3, 117.6, 115.7, 75.9, 68.4, 66.0, 31.7, 29.2, 29.0, 25.9, 22.5, 15.7, 14.0.

General Method for the Synthesis of Nitriles 4a-c.

To a solution of alcohols 3a-c (1.0 mmol) in a mixture of toluene (3 mL) and EtOAc (3 mL), a solution of NaBr (0.11 g, 1.1 mmol) in water (0.5 mL) was added followed by 2,2,6,6-tetramethylpiperidine-1-yloxy free radical (TEMPO) (2.2 mg, 0.01 mmol). To the resulting biphasic system, which was cooled at 0° C., an aqueous solution of 0.35 M NaOCl (3.1 mL, 1.1 mmol) containing NaHCO$_3$ (0.25 g, 3 mmol) was added dropwise under vigorous stirring, at 0° C. over a period of 1 h. After the mixture had been stirred for a further 15 min at 0° C., EtOAc (10 mL) and H$_2$O (10 mL) were added. The aqueous layer was separated and washed with EtOAc (2×10 mL). The combined organic layers were washed consecutively with 5% aqueous citric acid (10 mL) containing KI (0.04 g), 10% aqueous Na$_2$S$_2$O$_3$ (10 mL), and brine and dried over Na$_2$SO$_4$. The solvents were evaporated under reduced pressure and the residue was used without any further purification.

To a mixture of TBDMSCN (1.0 mmol, 141 mg), potassium cyanide (0.2 mmol, 13 mg), and 18-crown-6 (0.4 mmol, 106 mg) was added dropwise a solution of the aldehyde derived from alcohol 3a-c, according to the NaBr/TEMPO protocol mentioned above, (1.0 mmol) in CH$_2$Cl$_2$ at room temperature under nitrogen over 30 min. After addition was complete, the mixture was stirred overnight at room temperature. The organic solvent was evaporated under reduced pressure and the residue was purified by column chromatography [EtOAc-petroleum ether (bp 40-60° C.), 0.5:9.5].

2-((tert-Butyldimethylsilyl)oxy)-3-(4-(4-fluorophenoxy)phenoxy)propanenitrile (4a)

Yield 82%; White oil; $^1$H NMR (200 MHz, CDCl$_3$): δ 7.07-6.82 (m, 8H), 4.80 (t, J=6.4 Hz, 1H), 4.26-4.06 (m, 2H), 0.94 (s, 9H), 0.24 (s, 3H), 0.20 (s, 3H).

2-((tert-Butyldimethylsilyl)oxy)-3-(4-(hexylthio)phenoxy)butanenitrile (Mixture of Diastereomers) (4b)

Yield 34%; White oil; $^1$H NMR (200 MHz, CDCl$_3$): δ 7.30 (d, J=8.2 Hz, 2H), 6.85 (d, J=8.2 Hz, 2H), 5.37-5.28 (m, 1H), 4.57-4.48 (m, 1H), 2.83 (t, J=7.0 Hz, 2H), 1.71-1.18 (m, 11H), 1.00-0.82 (m, 12H), 0.30-0.06 (m, 6H); $^{13}$C NMR (50 MHz, CDCl$_3$): δ 156.9, 132.4, 132.3, 128.6, 118.4, 116.7, 116.5, 75.5, 74.7, 65.5, 65.2, 35.4, 35.3, 31.3, 29.2, 28.4, 25.4, 22.5, 15.4, 15.1, 14.0, −5.3, −5.4.

2-((tert-butyldimethylsilyl)oxy)-3-(4-(heptyloxy)phenoxy)butanenitrile (Mixture of Diastereomers) (4c)

Yield 78%; White oil; $^1$H NMR (200 MHz, CDCl$_3$): δ 6.95-6.76 (m, 4H), 4.66-4.47 (m, 1H), 4.46-4.25 (m, 1H), 3.92 (t, J=6.6 Hz, 2H), 1.88-1.64 (m, 2H), 1.56-1.17 (m, 11H), 1.00-0.82 (m, 12H), 0.27-0.09 (m, 6H); $^{13}$C NMR (50 MHz, CDCl$_3$): δ 154.2, 150.8, 117.8, 117.7, 115.3, 76.6, 75.7, 68.4, 65.3, 65.1, 31.7, 29.3, 29.0, 25.9, 25.4, 22.5, 15.5, 15.1, 14.0, −5.3, −5.4.

General Method for the Synthesis of Thiazolines 5a-c.

To a stirred solution of the nitriles 4a-c (1.0 mmol) and CH$_3$COO$^-$NH$_4$$^+$ (3.6 mmol, 277 mg) in MeOH (4 mL), HCl.H-L-Cys-OMe (3.0 mmol, 515 mg) was added, and the mixture was stirred overnight at room temperature. The organic solvent was evaporated under reduced pressure and the residue was purified by column chromatography [EtOAc-petroleum ether (bp 40-60° C.), 1:9].

Methyl 2-(1-((tert-butyldimethylsilyl)oxy)-2-(4-(4-fluorophenoxy)phenoxy)ethyl)-4,5-dihydrothiazole-4-carboxylate (Mixture of Diastereomers) (5a)

Yield 35%; White oil; $^1$H NMR (200 MHz, CDCl$_3$): δ 7.39-6.42 (m, 8H), 5.34-4.74 (m, 2H), 4.42-3.21 (m, 7H), 1.56-0.50 (m, 9H), 0.35-(−0.08) (m, 6H).

Methyl 2-(1-((tert-butyldimethylsilyl)oxy)-2-(4-(hexylthio)phenoxy)propyl)-4,5-dihydrothiazole-4-carboxylate (Mixture of Diastereomers) (5b)

Yield 19%; White oil; $^1$H NMR (200 MHz, CDCl$_3$): δ 7.40-7.17 (m, 2H), 6.96-6.68 (m, 2H), 5.28-5.03 (m, 1H), 4.90-4.77 (m, 1H), 4.76-4.56 (m, 1H), 3.79 (s, 3H), 3.58-3.28 (m, 2H), 2.79 (t, J=7.0 Hz, 2H), 1.70-1.11 (m, 11H), 1.01-0.78 (m, 12H), 0.19-0.01 (m, 6H); $^{13}$C NMR (50 MHz, CDCl$_3$): δ 179.8, 171.2, 156.4, 133.1, 132.7, 116.1, 78.3, 78.0, 76.4, 74.8, 74.6, 52.7, 35.9, 35.6, 33.8, 33.6, 31.3, 29.2, 28.4, 25.8, 25.7, 22.5, 18.2, 14.0, 13.9, −4.7, −5.3.

Methyl 2-(1-((tert-butyldimethylsilyl)oxy)-2-(4-(heptyloxy)phenoxy)propyl)-4,5-dihydrothiazole-4-carboxylate (Mixture of Diastereomers) (5c)

Yield 26%; Pale yellow oil; $^1$H NMR (200 MHz, CDCl$_3$): δ 6.92-6.73 (m, 4H), 5.25-5.05 (m, 1H), 4.89-4.76 (m, 1H), 4.69-4.49 (m, 1H), 3.89 (t, J=6.6 Hz, 2H), 3.83-3.75 (m, 3H), 3.55-3.30 (m, 2H), 1.86-1.63 (m, 2H), 1.50-1.10 (m, 11H), 1.06-0.75 (m, 12H), 0.17-0.01 (m, 6H).

General Method for the Synthesis of Thiazoles 6a-c.

To a solution of the thiazolines 5a-d (1 mmol) in CH$_2$Cl$_2$ (20 mL), BrCCl$_3$ (6.0 mmol, 0.59 mL) and DBU (6.0 mmol, 0.90 mL) were added at 0° C. The reaction was stirred for 2 h at 0° C. and overnight at room temperature. The organic solvent was evaporated under reduced pressure and the residue was purified by column chromatography [EtOAc-petroleum ether (bp 40-60° C.), 1:9].

Methyl 2-(1-((tert-butyldimethylsilyl)oxy)-2-(4-(4-fluorophenoxy)phenoxy)ethyl)thiazole-4-carboxylate (6a)

Yield 86%; White oil; $^1$H NMR (200 MHz, CDCl$_3$): δ 8.17 (s, 1H), 7.12-6.67 (m, 8H), 5.52-5.36 (m, 1H), 4.49-4.33 (m, 1H), 4.11-3.84 (m, 4H), 0.94 (s, 9H), 0.16 (s, 3H), 0.13 (s, 3H).

Methyl 2-(1-(tert-butyldimethylsilyloxy)-2-(4-(hexylthio)phenoxy)propyl)thiazole-4-carboxylate (Mixture of Diastereomers) (6b)

Yield 92%; White oil; $^1$H NMR (200 MHz, CDCl$_3$): δ 8.15 (s, 1H), 7.39-7.23 (m, 2H), 6.97-6.82 (m, 2H), 5.44-5.30 (m, 1H), 4.98-4.74 (m, 1H), 3.95 (s, 3H), 2.81 (t, J=7.0 Hz, 2H), 1.69-1.09 (m, 11H), 1.05-0.77 (m, 12H), 0.22-(−0.02) (m, 6H); $^{13}$C NMR (50 MHz, CDCl$_3$): δ 176.7, 161.2, 156.4, 146.9, 133.1, 132.8, 127.8, 116.2, 76.7, 74.7, 52.4, 35.6, 31.3, 29.2, 28.4, 25.8, 25.7, 25.5, 25.4, 22.5, 18.2, 14.0, 12.7, −4.5, −5.3.

Methyl 2-(1-((tert-butyldimethylsilyl)oxy)-2-(4-(heptyloxy)phenoxy)propyl)thiazole-4-carboxylate (Mixture of Diastereomers) (6c)

Yield 65%; White oil; $^1$H NMR (200 MHz, CDCl$_3$): δ 8.14 (s, 1H), 7.05-6.61 (m, 4H), 5.47-5.17 (m, 1H), 4.85-4.59 (m, 1H), 4.31-3.68 (m, 5H), 1.88-0.65 (m, 25H), 0.39-(−0.15) (m, 6H).

General Method for the Synthesis of 7a-c.

Compounds 6a-c (1.0 mmol) were treated with a solution of 2N HCl in MeOH (10 mL). After TLC indicated complete disappearance of the starting material, the organic solvent was evaporated under reduced pressure and the residue was recrystallized from ether/petroleum ether (bp 40-60° C.).

Methyl 2-(2-(4-(4-fluorophenoxy)phenoxy)-1-hydroxyethyl)thiazole-4-carboxylate (7a)

Yield 95%; White solid; $^1$H NMR (200 MHz, CDCl$_3$): δ 8.19 (s, 1H), 7.09-6.78 (m, 8H), 5.51-5.37 (m, 1H), 4.54-4.40 (m, 1H), 4.29-4.17 (m, 1H), 3.93 (s, 3H); $^{13}$C NMR (50 MHz, CDCl$_3$): δ 172.3, 161.7, 154.0, 151.4, 146.0, 136.2, 128.2, 120.0, 119.4, 119.2, 116.3, 115.9, 71.9, 70.7, 52.5.

Methyl 2-(2-(4-(hexylthio)phenoxy)-1-hydroxypropyl)thiazole-4-carboxylate (Mixture of Diastereomers) (7b)

Yield 87%; White oil; $^1$H NMR (200 MHz, CDCl$_3$): δ 8.19 (s, 1H), 7.32 (d, J=8.8 Hz, 2H), 6.91 (d, J=8.8 Hz, 2H), 5.32 (d, J=4.0 Hz, 1H), 4.95-4.80 (m, 1H), 3.95 (s, 3H), 2.83 (t, J=7.2 Hz, 2H), 1.69-1.50 (m, 2H), 1.49-1.12 (m, 9H), 0.88 (t, J=6.6 Hz, 3H).

General Method for the Synthesis of Thiazolyl Ketones 8a-c.

To a solution of compounds 7a-c, (1 mmol) in dry CH$_2$Cl$_2$ (10 mL), Dess-Martin periodinane was added (1.5 mmol, 637 mg) and the mixture was stirred for 1 h at room temperature. The organic solvent was evaporated under reduce pressure and Et$_2$O (30 mL) was added. The organic phase was washed with saturated aqueous NaHCO$_3$ (20 mL) containing Na$_2$S$_2$O$_3$ (1.5 g, 9.5 mmol), H$_2$O (20 mL), dried over Na$_2$SO$_4$, and the organic solvent was evaporated under reduced pressure. The residue was purified by column chromatography using petroleum ether (bp 40-60° C.)/EtOAc as eluent.

Methyl 2-(2-(4-(4-fluorophenoxy)phenoxy)acetyl)thiazole-4-carboxylate (8a, GK440)

Yield 85%; White solid; $^1$H NMR (600 MHz, CDCl$_3$): δ 8.52 (s, 1H), 7.03-6.90 (m, 8H), 5.59 (s, 2H), 4.01 (s, 3H); $^{13}$C NMR (150 MHz, CDCl$_3$): δ 187.5, 164.4, 161.0, 159.3, 157.7, 153.8, 151.8, 148.7, 133.6, 120.0, 119.5, 116.3, 116.1, 70.9, 52.8; HRMS (ESI) calcd for C$_{19}$H$_{14}$FNNaO$_5$S [M+Na]$^+$: 410.0469. Found: 410.0477.

Methyl 2-(2-(4-(hexylthio)phenoxy)propanoyl)thiazole-4-carboxylate (8b, GK449)

Yield 89%; Yellow solid; $^1$H NMR (600 MHz, CDCl$_3$): δ 8.44 (s, 1H), 7.19 (d, J=9.0 Hz, 2H), 6.77 (d, J=9.0 Hz, 2H), 5.97 (q, J=7.2 Hz, 1H), 3.93 (s, 3H), 2.72 (t, J=7.2 Hz, 2H), 1.68 (d, J=7.2 Hz, 3H), 1.52-1.45 (m, 2H), 1.34-1.26 (m, 2H), 1.24-1.14 (m, 4H), 0.80 (t, J=6.6 Hz, 3H); $^{13}$C NMR (150 MHz, CDCl$_3$): δ 191.4, 164.7, 161.1, 156.2, 148.8, 133.9, 132.4, 128.5, 116.1, 75.0, 52.7, 35.4, 31.3, 29.3, 28.4, 22.5, 18.6, 14.0; HRMS (ESI) calcd for C$_{20}$H$_{26}$NO$_4$S$_2$ [M+H]$^+$: 408.1298. Found: 408.1291.

Methyl 2-(2-(4-(heptyloxy)phenoxy)propanoyl)thiazole-4-carboxylate (8c, GK439)

Yield 87%; Pale yellow solid; $^1$H NMR (600 MHz, CDCl$_3$): δ 8.50 (s, 1H), 6.88 (d, J=9.0 Hz, 2H), 6.78 (d, J=9.0 Hz, 2H), 5.96 (q, J=6.6 Hz, 1H), 4.01 (s, 3H), 3.87 (t, J=6.6 Hz, 2H), 1.77-1.70 (m, 5H), 1.64-1.53 (m, 2H), 1.46-1.39 (m, 2H), 1.37-1.24 (m, 4H), 0.89 (t, J=6.6 Hz, 3H); $^{13}$C NMR (150 MHz, CDCl$_3$): δ 191.9, 164.9, 161.1, 154.1, 151.2, 148.7, 133.7, 117.0, 115.4, 76.0, 68.5, 52.7, 31.8, 29.3, 29.0, 26.0, 22.6, 18.6, 14.1; HRMS (ESI) calcd for C$_{21}$H$_{27}$NNaO$_5$S [M+Na]$^+$: 428.1502. Found: 428.1514.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The invention claimed is:
1. A compound of the formula:
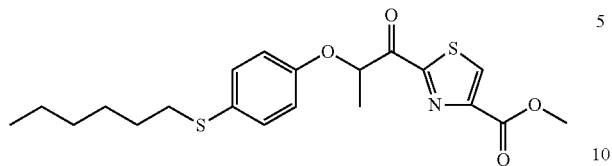
or a salt thereof.

UNITED STATES PATENT AND TRADEMARK OFFICE
CERTIFICATE OF CORRECTION

PATENT NO. : 10,150,781 B2
APPLICATION NO. : 15/501141
DATED : December 11, 2018
INVENTOR(S) : Berit Johansen et al.

It is certified that error appears in the above-identified patent and that said Letters Patent is hereby corrected as shown below:

On the Title Page

Item (72) Delete "Sanderberg" and insert -- Sandberg --.

Signed and Sealed this
Seventeenth Day of March, 2020

Andrei Iancu
*Director of the United States Patent and Trademark Office*